(12) United States Patent
Nishihara et al.

(10) Patent No.: US 10,441,182 B2
(45) Date of Patent: Oct. 15, 2019

(54) MAGNETIC RESONANCE IMAGING APPARATUS AND MAGNETIC RESONANCE IMAGING METHOD

(71) Applicant: HITACHI, LTD., Tokyo (JP)

(72) Inventors: Takashi Nishihara, Tokyo (JP); Hiroyuki Itagaki, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 949 days.

(21) Appl. No.: 14/904,152

(22) PCT Filed: Jul. 8, 2014

(86) PCT No.: PCT/JP2014/068099
§ 371 (c)(1),
(2) Date: Jan. 11, 2016

(87) PCT Pub. No.: WO2015/005297
PCT Pub. Date: Jan. 15, 2015

(65) Prior Publication Data
US 2016/0143545 A1    May 26, 2016

(30) Foreign Application Priority Data
Jul. 12, 2013  (JP) ................................ 2013-146818

(51) Int. Cl.
*A61B 5/026* (2006.01)
*A61B 5/055* (2006.01)
(Continued)

(52) U.S. Cl.
CPC ............ *A61B 5/0263* (2013.01); *A61B 5/055* (2013.01); *A61B 5/113* (2013.01); *A61B 5/4244* (2013.01);
(Continued)

(58) Field of Classification Search
None
See application file for complete search history.

(56) References Cited

U.S. PATENT DOCUMENTS

| | | | |
|---|---|---|---|
| 6,560,477 B1* | 5/2003 | Filler ...................... | A61B 5/055 324/309 |
| 2002/0095085 A1* | 7/2002 | Saranathan ............ | A61B 5/055 600/413 |

(Continued)

FOREIGN PATENT DOCUMENTS

| | | |
|---|---|---|
| JP | 2011-92678 A | 5/2011 |
| JP | 2013-31633 A | 2/2013 |

(Continued)

OTHER PUBLICATIONS

International Search Report from International Application No. PCT/JP14/68099 dated Oct. 21, 2014.

*Primary Examiner* — Jason T Yen
(74) *Attorney, Agent, or Firm* — Brundidge & Stanger, P.C.

(57) ABSTRACT

Provided is a technique in MRI to efficiently suppress downstream blood in a specific region in a blood vessel having a slow flow velocity, such as the portal vein. For this purpose, a plurality of Beam Sat pulses are applied so as to equally suppress signals of blood flowing into a desired imaging region from a desired blood vessel during the period from applying an IR pulse to starting main imaging. Downstream blood in a specific region in a blood vessel having a slow flow velocity, such as the portal vein, can be suppressed efficiently by determining application conditions of the plurality of Beam Sat pulses that achieve the above based on a flow velocity of blood in a desired blood vessel and T1 of the said blood.

14 Claims, 19 Drawing Sheets

(51) Int. Cl.
*A61B 5/00* (2006.01)
*G01R 33/483* (2006.01)
*G01R 33/56* (2006.01)
*G01R 33/565* (2006.01)
*G01R 33/567* (2006.01)
*A61B 5/113* (2006.01)

(52) U.S. Cl.
CPC ..... *G01R 33/4836* (2013.01); *G01R 33/5607* (2013.01); *G01R 33/5673* (2013.01); *G01R 33/56509* (2013.01)

(56) References Cited

U.S. PATENT DOCUMENTS

2010/0226556 A1* 9/2010 Kumai .............. G01R 33/5614
382/131
2015/0161784 A1* 6/2015 Ma .................... G06K 9/6215
382/131

FOREIGN PATENT DOCUMENTS

WO      2012/043198   A1    4/2012
WO      2012/098955   A1    7/2012

\* cited by examiner

FIG.2
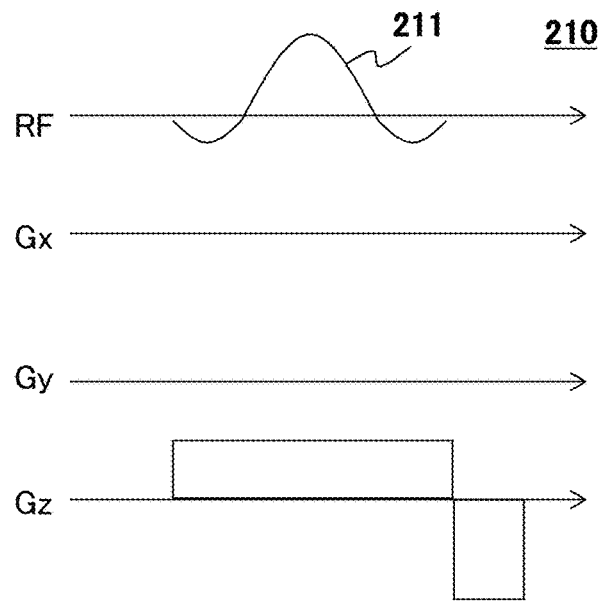
(a)
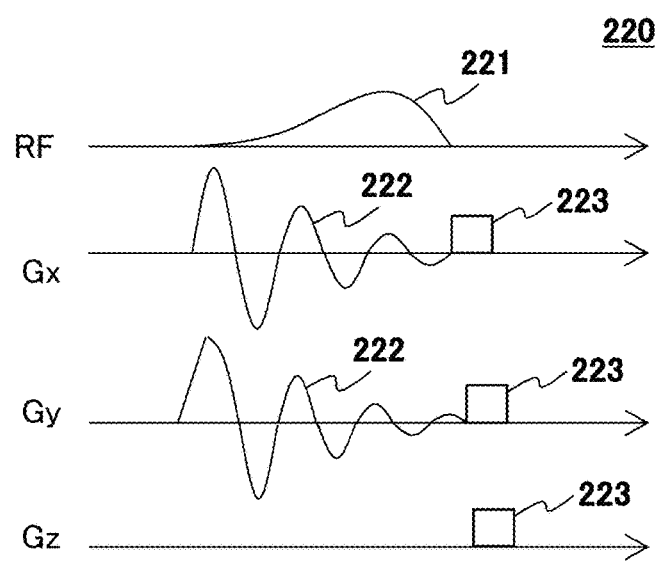
(b)

FIG.14
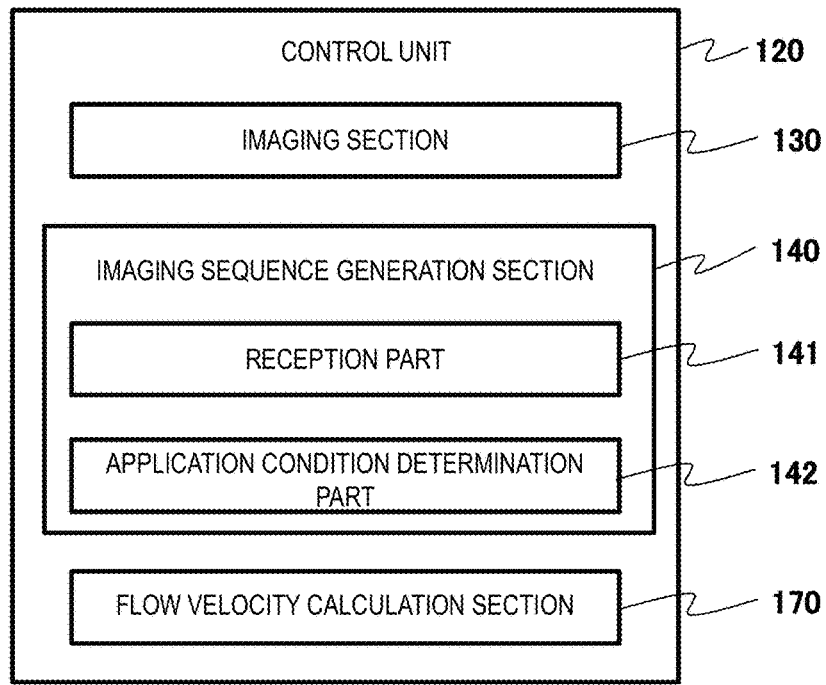
(a)
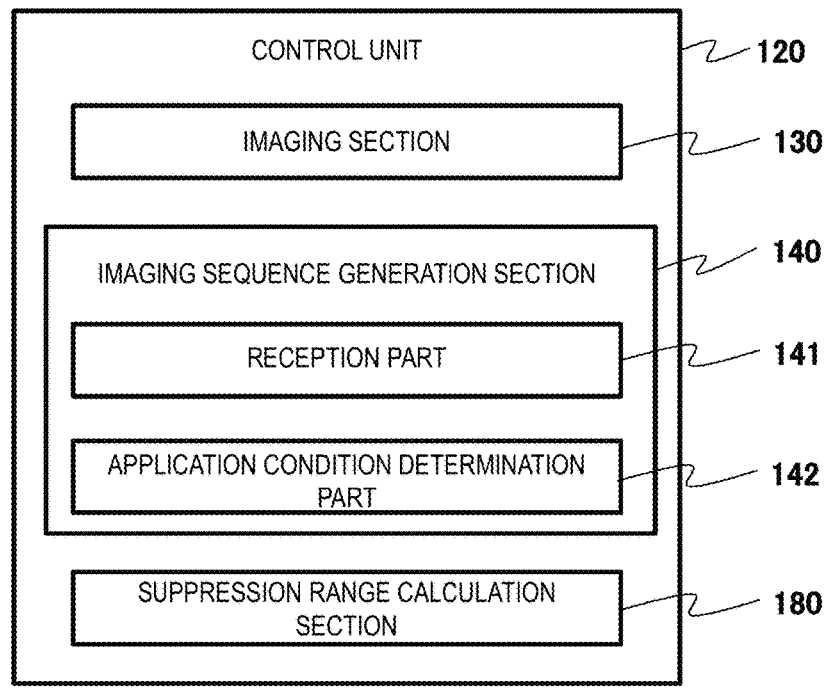
(b)

MAGNETIC RESONANCE IMAGING APPARATUS AND MAGNETIC RESONANCE IMAGING METHOD

TECHNICAL FIELD

The present invention relates to the Magnetic Resonance Imaging (hereinafter, referred to as MRI) technique and, in particular, to a technique for obtaining hemodynamic information in combination of an IR (Inversion Recovery) pulse and a two-dimensional selective RF pulse (hereinafter, referred to as a 2DRF pulse).

BACKGROUND ART

When liver cirrhosis progresses and an artery aneurysm is formed by blood in the portal vein flowing into the esophageal vein or the like, which increase the risk of esophageal varix rupture or the like. Therefore, it is necessary to visualize the portal system.

In order to visualize blood with an MRI apparatus, there is a method using an IR pulse. For example, entire magnetization is inverted using a first IR pulse that does not perform slice selection, and then a second slice selective IR pulse that performs slice selection is applied so that the regional blood flowing into an imaging surface is recovered from the magnetization. Then, imaging is performed after timings (TI) where the magnetization of the background tissue in the imaging surface becomes Null (for example, refer to Non-patent Literature 1).

Hence, the background tissue is suppressed, and additionally, and the blood flowed into the imaging surface between TIs can be visualized at a high signal.

Also, there is a method for applying a slice selective IR pulse to an imaging surface and imaging after a timing (TI) at which the magnetization of the background tissue becomes Null using the same IR pulse (for example, refer to Non-patent Literature 2).

Hence, the background tissue is suppressed, and additionally, blood flowed into an imaging surface between TIs is visualized at a high signal.

Also, the TOF imaging (Selective TOF MRA) in which a 2D RF pulse is applied as a pre-saturation pulse (Beam Sat pulse) to check a dominant region of a certain blood vessel is also known as the other blood vessel visualization method (for example, refer to Non-patent Literature 3).

CITATION LIST

Non-Patent Literature

NPTL 1: Hitoshi Kanazawa and Mitsue Miyazaki, et al., "Time-Spatial Labeling Inversion Tag (t-SLIP) using a Selective IR-Tag ON/OFF Pulse in 2D and 3D half-Fourier FSE as Arterial Spin Labeling" Proc. Intl. Soc. Mag. Reson. Med. 10 (2002)
NPTL 2: Isao Kanamori, Akitoshi Fujino, and Masami Niwa, "MRI of practice" (2011) p. 321-324
NPTL 3: Takashi Nishihara, et al., "Selective TOF MRA using Beam Saturation pulse", Proc. ISMRM 2012, 2497

SUMMARY OF INVENTION

Technical Problem

The blood vessel visualization method using an IR pulse disclosed in Non-patent Literature 1 or 2 needs to apply an IR pulse to a large region in order to perform labeling for all blood flowing into the region. For example, if an IR pulse is applied to a narrow range in a regionally selective manner in order to visualize a dominant region of a certain blood vessel, and this results in an insufficient amount of blood to be labeled, which reduces the blood vessel visualization ability. Therefore, the details of the blood path and the flow velocity cannot be checked sufficiently. Also, although a blood flow path can be visualized in Selective TOF MRA disclosed in Non-patent Literature 3, it is difficult to visualize blood in the portal system where the blood flow velocity is slow compared to the head and the blood flow direction is complicated.

For example, although only blood in a certain region can be suppressed by combining the blood vessel visualization method using an IR pulse with a slice-selective type of pre-saturation pulse, only a certain blood vessel with a complicated structure such as a portal vein cannot be suppressed selectively. On the other hand, only a certain blood vessel can be suppressed selectively by applying the Beam Sat pulse disclosed in Non-patent Literature 3 to the blood vessel visualization method using an IR pulse. However, because the region to be suppressed is narrow, blood that is not suppressed by the Beam Sat pulse flows into the imaging region, only partial blood is suppressed, and the downstream blood cannot be suppressed. It is particularly unsuitable for TOF to visualize blood vessels of the portal system where the blood flow velocity is slow and the blood flow direction is complicated.

The present invention was made in light of the above problems and has a purpose to provide a technique in MRI for efficiently suppressing downstream blood in a certain region in a blood vessel such as a portal vein with a slow blood flow velocity.

Solution to Problem

The present invention combines a blood vessel visualization method using an IR pulse with a method in which a Beam Sat pulse is applied to a certain blood vessel as a pre-saturation pulse. At this time, in order to visualize hemodynamics of a desired blood vessel, a plurality of Beam Sat pulses are applied so that signals of blood flowing into a desired imaging region from the said blood vessel are equally suppressed between the IR pulse application and the start of main imaging. Application conditions of the plurality of the Beam Sat pulses achieving the above are determined based on a blood flow velocity in a desired blood vessel and the said blood T1.

Advantageous Effects of Invention

According to the present invention, downstream blood in a certain region can be suppressed efficiently in a blood vessel such as a portal vein with a slow blood flow velocity.

BRIEF DESCRIPTION OF DRAWINGS

FIG. 2(a) is an explanatory diagram for explaining a slice selective excitation sequence, and FIG. 2(b) is an explanatory diagram for explaining a 2D RF sequence.

FIG. 14(a) is a functional block diagram of the control unit of the fifth embodiment, and FIG. 14(b) is a functional block diagram of the control unit in a variation of the fifth embodiment.

DESCRIPTION OF EMBODIMENTS

First Embodiment

Figure 1:
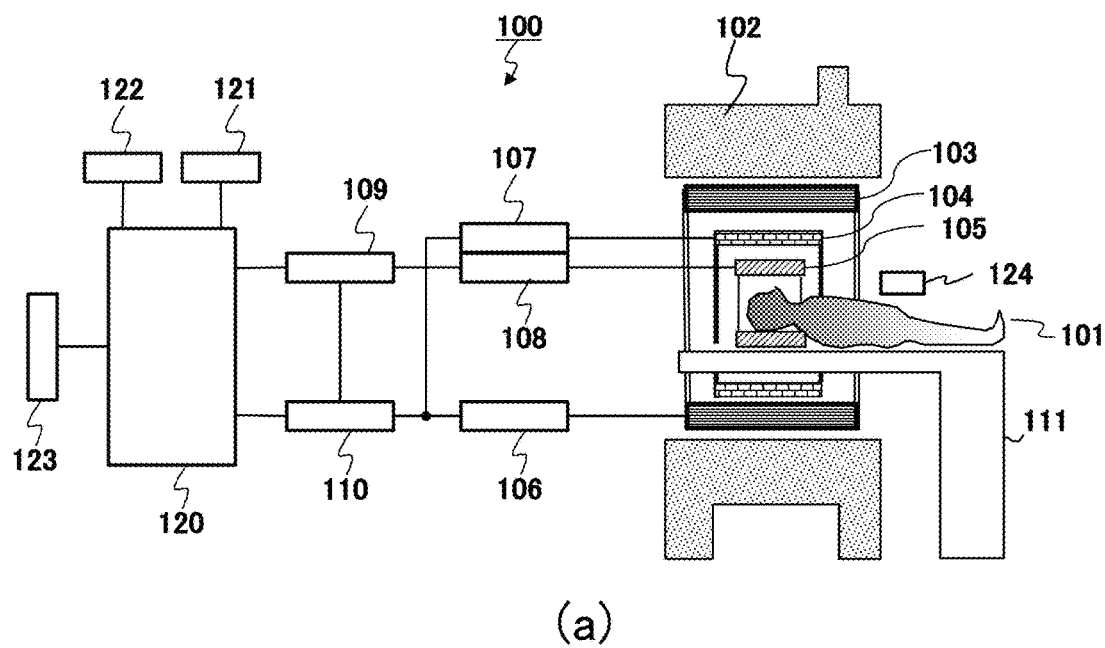
FIG. 1(a) is a block diagram of the MRI apparatus of the first embodiment.
FIG. 1(b) is a functional block diagram of the control unit.

Hereinafter, the first embodiment applying the present invention will be described. In all the diagrams for explaining the embodiments of the present invention, the same symbols are provided basically for the same functions, and the repeated explanations will be omitted.

First, the configuration of the MRI apparatus of the present embodiment will be described. FIG. 1(a) is a block diagram of the MRI apparatus 100 of the present embodiment. The MRI apparatus 100 of the present embodiment is an apparatus that obtains a tomographic image of an object 101 using the NMR phenomenon. As shown in FIG. 1(a), the static magnetic field generating magnet 102, the gradient magnetic field coil 103, the gradient magnetic field power sources 106, the transmission RF coil (transmission coil) 104, the RF transmission unit 107, the reception RF coil (reception coil) 105, the signal detection unit 108, the signal processing unit 109, the sequencer 110, the control unit 120, the display unit 121, the operation unit 122, the storage unit 123, and the bed 111 that places the object 101 and carries the object 101 out of/in the inside of the static magnetic field generating magnet 102 are included.

The static magnetic field generating magnet 102 functions as a static magnetic field generating unit generating a static magnetic field. The static magnetic field generating magnet 102 generates a homogeneous static magnetic field respectively in a direction orthogonal to the body axis of the object 101 in case of the vertical magnetic field system or in the body axis in case of the horizontal magnetic field system, and a static magnetic field generation source of the permanent magnet system, the normal conduction system, or the superconducting system is disposed near the object 101.

The gradient magnetic field coil 103 and the gradient magnetic field power sources 106 function as a gradient magnetic field application unit applying a gradient magnetic field to the object 101 disposed in a static magnetic field. The gradient magnetic field coil 103 is coils wound in the three axis directions X, Y, and Z that are the real space coordinate system (static coordinate system) of the MRI apparatus. The respective gradient magnetic field coils are connected to the gradient magnetic field power sources 106 that drive them and to which an electric current is supplied. Specifically, the gradient magnetic field power sources 106 of the respective gradient magnetic field coils are respectively driven according to the command from the sequencer 110 to be described later and supply an electric current to the respective gradient magnetic field coils. Hence, the gradient magnetic fields Gx, Gy, and Gz are generated in the three axis directions X, Y, and Z.

For example, when imaging a two-dimensional slice plane, a slice gradient magnetic field pulse (Gs) is applied in a direction orthogonal to a slice plane (cross section to be imaged), which sets the slice plane for the object 101. A phase-encoding gradient magnetic field pulse (Gp) and a frequency encoding (readout) gradient magnetic field pulse (Gf) are applied in the other two directions that are orthogonal to the slice plane and are orthogonal to each other, and then positional information in the respective directions are encoded for an echo signal.

The transmission coil 104 and the RF transmission unit 107 function as a high-frequency magnetic field transmission unit transmitting a high-frequency pulse (RF pulse) that excites magnetization of the object 101 at a predetermined flip angle. The transmission coil 104 is a coil to irradiate an RF pulse to the object 101 and is connected to the RF transmission unit 107, and an RF pulse current is supplied from the RF transmission unit 107. By irradiating an RF pulse to the object 101 from the transmission coil 104, the NMR phenomenon is induced to nuclear spins of atoms composing biological tissues of the object 101.

Specifically, the RF transmission unit 107 is driven according to the command from the sequencer 110 to be described later, performs amplitude modulation for a high-frequency pulse, and the high-frequency pulse is amplified and supplied to the transmission coil 104 disposed in the vicinity of the object 101. The supplied high-frequency pulse is irradiated to the object 101 from the transmission coil 104.

The reception coil 105 and the signal detection unit 108 function as a signal reception unit receiving an echo signal generated by the object 101. The reception coil 105 is a coil to receive an NMR signal (echo signal) emitted by the NMR phenomenon of nuclear spins composing biological tissues of the object 101, is connected to the signal detection unit 108, and transmits a received echo signal to the signal detection unit 108. The signal detection unit 108 performs a detection process for the echo signal received by the reception coil 105.

Specifically, a responding echo signal of the object 101 induced by an RF pulse irradiated from the transmission coil 104 is sent to the signal detection unit 108 after being received in the reception coil 105 disposed in the vicinity of the object 101. The signal detection unit 108 amplifies a received echo signal according to the command from the sequencer 110 to be described later, divides the echo signal into orthogonal two-system signals by quadrature phase detection, samples each signal in a predetermined number (for example, 128, 256, 512, or the like), performs A/D conversion for each sampled signal into a digital amount, and then sends it to the signal processing unit 109 to be described later. Thus, an echo signal is obtained as time-series digital data (hereinafter, referred to as echo data) comprised of the predetermined number of sampling data.

The signal processing unit 109 performs various signal processes for echo data and sends the processed echo data to the control unit 120.

The sequencer 110 transmits various commands for data collection required for reconstructing a tomographic image of the object 101 mainly to the gradient magnetic field power sources 106, the RF transmission unit 107, and the signal detection unit 108 and controls them. Specifically, the sequencer 110 operates by control of the control unit 120 to be described later, controls the gradient magnetic field power sources 106, the RF transmission unit 107, and the signal detection unit 108 according to the imaging sequence, applies an RF pulse and a gradient magnetic field pulse to the object 101, repeats detection of an echo signal from the object 101, and then collects echo data required for reconstructing an image in an imaging region of the object 101.

The control unit 120 controls the sequencer 110, processes various data, displays process results, performs control such as storage, and includes a CPU and a memory inside. In the present embodiment, an image is reconstructed from an echo signal received by the above signal reception unit, and commands to control operations of a gradient magnetic field application unit, high-frequency magnetic field transmission unit, and signal reception unit are provided to the sequencer 110 according to the imaging sequence. Additionally, the imaging sequence is generated by imaging parameters set by a user and a pulse sequence specified by a user.

The control unit 120 of the present embodiment specifically controls the sequencer 110 to execute echo data collection and stores the collected echo data in a region equivalent to k-space of a memory based on encoding information applied to the echo data. An echo data group stored in the region equivalent to k-space of a memory is also referred to as k-space data. Then, a signal process for the k-space data and a process such as image reconstruction by the Fourier transform are executed, and the result image of the object 101 is displayed on the display unit 121 to be described later and is recorded in the storage unit 123.

The display unit 121 and the operation unit 122 are interfaces to communicate various control information of the MRI apparatus 100, information required for arithmetic processing, and the arithmetic processing results with a user. The MRI apparatus 100 of the present embodiment receives an input from a user through the display unit 121 and the operation unit 122. The operation unit 122 is disposed in the vicinity of the display unit 121 and controls various processes of the MRI apparatus 100 interactively through the operation unit 122 by an operator checking the display unit 121. For example, the display unit 121 displays a reconstructed image of the object 101. Also, the operation unit 122 is provided with at least one of input devices such as a trackball, a mouse, and a keyboard.

The storage unit 123 stores information required for operations of the MRI apparatus 100, data while being processed, and the like. For example, the storage unit 123 is comprised of an optical disk, a magnetic disk, or the like.

Additionally, in FIG. 1(*a*), the transmission coil 104 and the gradient magnetic field coil 103 are installed in the static magnetic field space of the static magnetic field generating magnet 102 where the object 101 is to be inserted so that they are opposite to the object 101 in case of the vertical magnetic field system or so that they surround the object 101 in case of the horizontal magnetic field system. Also, the reception coil 105 is installed so that it is opposite to or surrounds the object 101.

Also, for example, in case of imaging in synchronization with periodic body motion of the object 101 similarly to respiration synchronized imaging, the body motion detection device 124 that detects the periodic body motion of the object 101 may be further provided. The body motion detection device 124 is installed in a position where body motion of the object 101 to be detected can be detected. The detected body motion information is sent to the control unit 120.

A clinically prevalent nuclide to be imaged by the MRI apparatus 100 is a hydrogen nucleus (proton) that is a main structural component of the object 101. The MRI apparatus 100 two- or three-dimensionally images shapes or functions of the human head, abdomen, extremities, and the like by imaging information about spatial distribution of the proton density and spatial distribution of the relaxation time of an excitation state. At this time, in MRI, an RF pulse is applied together with a gradient magnetic field in order to excite only protons in a certain region.

As the certain region, FIG. 2(*a*) shows an example of the pulse sequence (slice selective excitation sequence) 210 in case of selectively exciting an arbitrary slice having a thickness in the one-dimensional direction. Hereinafter, RF, Gx, Gy, and Gz in the pulse sequence diagrams of the present description shows application timings of an RF pulse, a gradient magnetic field in the x-axis direction, a gradient magnetic field in the y-axis direction, and a gradient magnetic field in the z-axis direction respectively.

In the slice selective excitation sequence 210, as shown in the present diagram, the slice selective gradient magnetic field 212 is applied in any one direction of Gx, Gy, and Gz at the same time as the RF pulse 211. Here, the application in the Gz direction is shown as an example. Hence, a predetermined slice in which only a position in the z-axis direction is specified is excited selectively.

Also, as the certain region, FIG. 2(*b*) shows an example of the pulse sequence in case of selectively exciting a region two- or three-dimensionally. Here, as an example, the two-dimensional spatial selective excitation sequence (2D RF sequence) 220 that selectively excites a region two-dimensionally is shown.

As shown in the present diagram, the 2D RF sequence 220 includes the two-dimensional selective excitation pulse (hereinafter, referred to as a 2D RF pulse) 221 and the vibration gradient magnetic field pulse 222. Here, a case where the vibration gradient magnetic field pulse 222 is applied in the Gx and Gy directions is shown as an example. By these 2D RF pulse 221 and the vibration gradient magnetic field pulse 222, only a certain cylindrical region is excited selectively. Additionally, the 2D RF pulse 221 is a pencil beam type of excitation RF pulse that excites a cylindrical region.

Generally, when a crusher gradient magnetic field pulse is applied after an RF pulse, a signal of a region to which the RF pulse was applied is suppressed. In the 2D RF sequence 220 of the present embodiment, the crusher gradient magnetic field pulse 223 is applied to the respective gradient magnetic field application axes after applying the vibration gradient magnetic field pulse 222.

Blood magnetization in a certain blood vessel is suppressed by combining the 2D RF pulse 221 with the vibration gradient magnetic field pulse 222 and the crusher gradient magnetic field pulse 223 to apply as a pre-saturation pulse and performing TOF imaging, which can check a dominant region of the blood vessel. Hereinafter, in the present description, a set of the 2D RF pulse 221, the vibration gradient magnetic field pulse 222, and the crusher gradient magnetic field pulse 223 to be applied as a pre-saturation pulse is referred to as a Beam Sat pulse.

In the present embodiment, a blood vessel visualizing method using an IR pulse is combined with a method of applying a Beam Sat pulse to a certain blood vessel as a pre-saturation pulse. At this time, in order to visualize hemodynamics of a desired blood vessel, a plurality of Beam Sat pulses are applied so that signals of blood flowing from the said desired blood vessel to a desired imaging region are equally suppressed between the IR pulse application and the main imaging start. Application conditions of the plurality of Beam Sat pulses to achieve this are determined based on a blood flow velocity in a desired blood vessel and the said blood T1.

Figure 3:
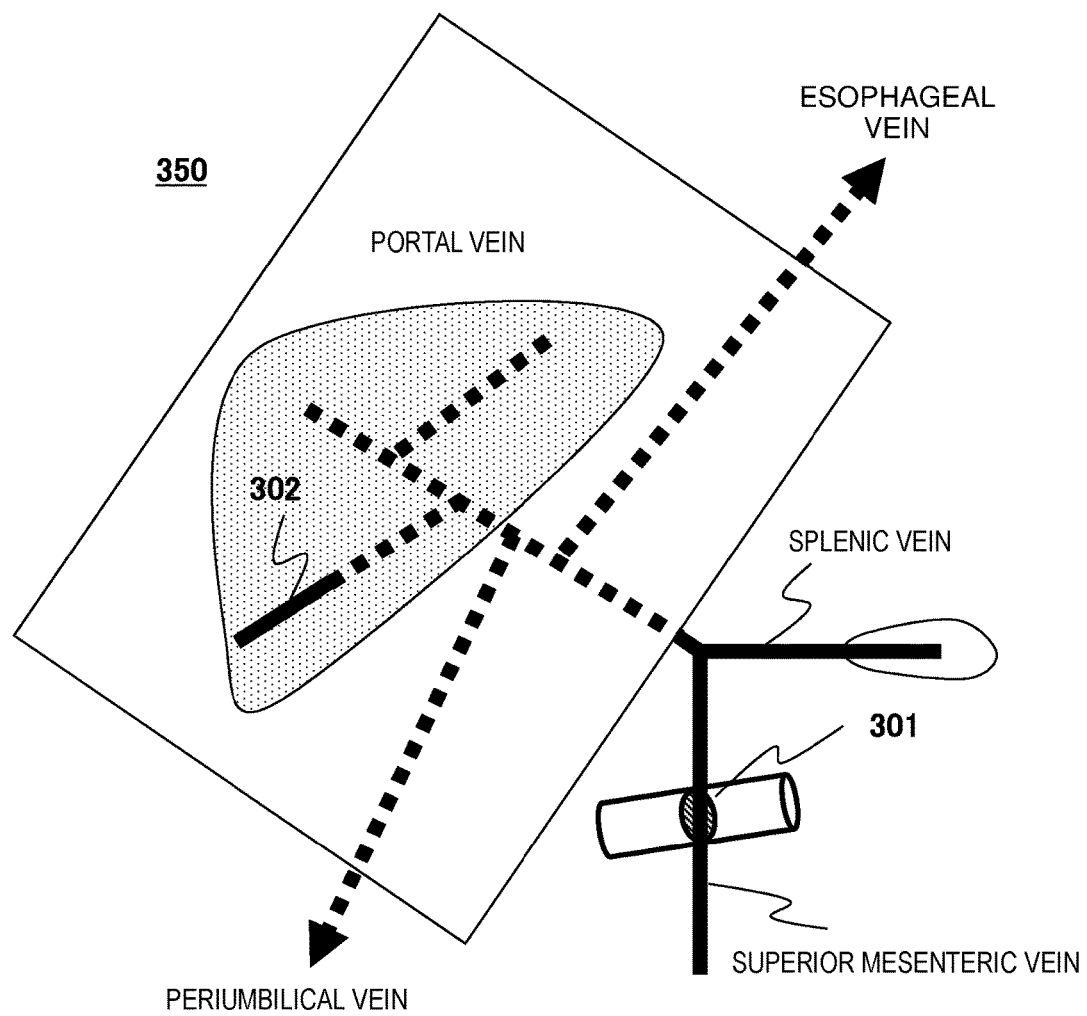
FIG. 3 is an explanatory diagram for explaining a blood flow to be suppressed in the first embodiment.

In the present embodiment, a case where an imaging target is the portal vein of the liver as shown in FIG. 3 will be described as an example. As shown in the present diagram, blood flows into the portal vein of the imaging region from the superior mesenteric vein, the splenic vein, and the like. Also, all the blood flowing into the liver region from these veins does not necessarily flow into the portal vein and flows also to the esophageal vein, the periumbilical vein, and the like. In the present embodiment, for example, a plurality of Beam Sat pulses are applied to a predetermined region on the superior mesenteric vein in the period between the IR pulse application and the main imaging start in order to surely suppress only blood flowing from the superior mesenteric vein to the portal vein, which can observe the hemodynamics.

In order to achieve this, the control unit 120 of the present embodiment, as shown in FIG. 1(b), collects echo signals from an imaging region according to the imaging sequence and includes the imaging section 130 that reconstructs an image from the said echo signals and the imaging sequence generation section 140 that applies imaging conditions to a predetermined pulse sequence to generate the imaging sequence.

The imaging section 130 controls each portion of the MRI apparatus 100 according to the imaging sequence generated by the imaging sequence generation section 140 or the predetermined imaging sequence and executes imaging.

Specifically, the imaging section 130 provides commands to the sequencer 110 according to the imaging sequence to obtain an echo signal. Then, the Fourier transform is provided for the obtained echo signal in order to reconstruct an image. The present embodiment performs blood vessel imaging and positioning image acquisition imaging.

Figure 4:
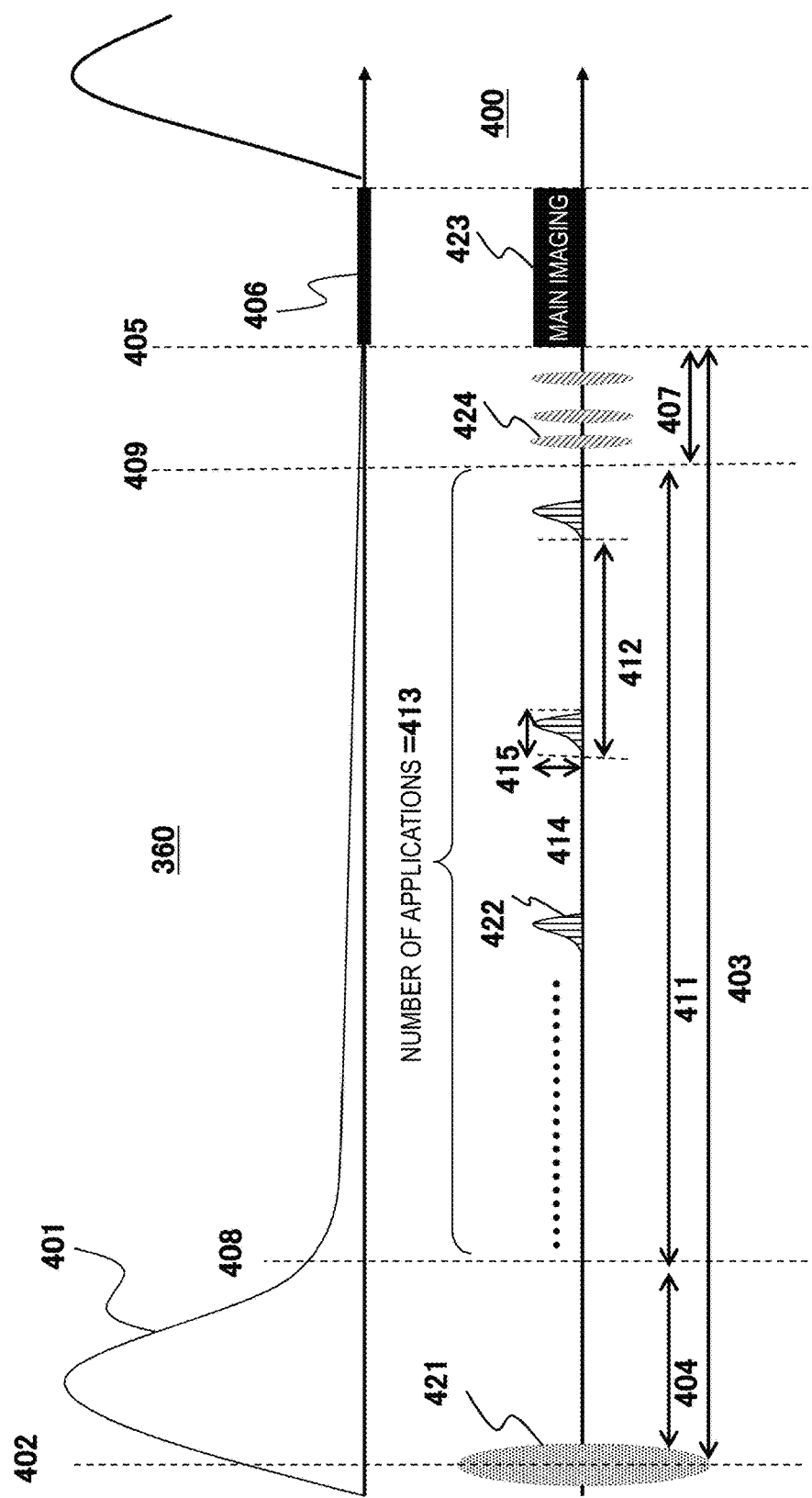
FIG. 4 is an explanatory diagram for explaining an example of the pulse sequence of the first embodiment.

The pulse sequence 400 used in the present embodiment is comprised of the IR (Inversion Recovery) pulse 421 and a plurality of the Beam Sat pulses (two-dimensional selective high-frequency pulses) 422 as shown in FIG. 4. In the present embodiment, the IR pulse 421 is synchronized with the respiratory motion (the respiratory waveform 401) and applied, and the plurality of the Beam Sat pulses 422 are applied during the TI period 403 between the IR pulse 421 and the main imaging 423.

Also, the imaging sequence generation section 140 is provided with the reception part 141 that receives imaging conditions including application conditions of the plurality of the Beam Sat pulses (two-dimensional selective high-frequency pulses) 422 from a user and the application condition determination part 142 that determines the application conditions (applied application conditions) used in an imaging sequence from the application conditions (set application conditions) of the plurality of the Beam Sat pulses (two-dimensional selective high-frequency pulses) 422 set as the imaging conditions. At this time, the application condition determination part 142 determines the applied application conditions so as to suppress the echo signal from blood in a desired blood vessel.

Additionally, in the present description, application conditions to be determined by the application condition determination part 142 include the total application time 411 and the application interval 412 of the plurality of the Beam Sat pulses (two-dimensional selective high-frequency pulses) 422 as well as the amplitude 414 and the pulse width 415 of each Beam Sat pulse (two-dimensional selective high-frequency pulse) 422.

The reception part 141 displays a screen that is to be a user interface on the display unit 121 and receives application conditions of a plurality of the Beam Sat pulses 422 through the said screen. At this time, an example of the screen to be displayed as a user interface will be described using FIGS. 3 and 4.

A display example of an application position reception screen will be described using FIG. 3. The positioning image 350 obtained by the imaging section 130 is displayed on the application position reception screen. A user specifies a blood vessel to be suppressed on the positioning image 350 and sets the application position 301 of the Beam Sat pulse 422. Additionally, a region to be suppressed may be displayed clearly by a method such as hatching the region (periphery) 302 to be suppressed by the Beam Sat pulse 422. The reception part 141 receives the application position 301 of the Beam Sat pulse 422 on the positioning image 350 in the application position reception screen.

The Beam Sat pulse setting screen display example 360 will be described using FIG. 4. In the present embodiment, respiration synchronized imaging is performed. Therefore, the respiratory waveform 401, the IR pulse 421, the application timing 402, the start timing 405 of the main imaging 423, and the execution period 406 in the pulse sequence 400 are displayed on the Beam Sat pulse setting screen display example 360.

In case of applying the pre-pulse 424 other than the Beam Sat pulse 422 before the main imaging 423, the application period 407 is also displayed.

A user sets the total application time 411 of the Beam Sat pulses 422, the application interval 412, the amplitude 414, and the pulse width 415 through this screen. The reception part 141 receives the settings by the user as the set application conditions.

Also, in the diagram, 413 is the number of applications by the Beam Sat pulse 422, 408 is the application start timing of the Beam Sat pulse 422, and 409 is the application end timing. Also, 403 is the time from applying the IR pulse 421 to starting the main imaging 423. In case of not applying the Beam Sat pulse 422, the blood flowing into an imaging region meanwhile is visualized at a high signal. Also, 404 is the time from applying the IR pulse 421 to starting application of the Beam Sat pulse 422. The blood flowing meanwhile is visualized at a high signal because it is not suppressed by the Beam Sat pulse 422.

Additionally, application conditions related to a plurality of the Beam Sat pulses 422 that is set by a user are not limited to the total application time 411 and the application interval 412. Two of the total application time 411, the application interval 412, and the number of application times 413 should be set.

Additionally, the initial values of application conditions of the Beam Sat pulse 422 are stored in the storage unit 123, and it may be configured so that the initial values are displayed and adjusted by a user. For example, the adjustment may be configured so as to perform by inputting values directly or may be configured so as to display a slide bar etc. and receive the operation.

Additionally, the initial values to be stored may be associated with, for example, an imaging site, a blood vessel to be suppressed, and the like.

The application condition determination part 142 of the present embodiment determines whether or not to apply set application conditions of a Beam Sat pulse received by the reception part 141 and decides the application conditions to be eventually used for imaging. Specifically, the application condition determination part 142 suppresses blood in a desired range as well as determines the total application time 411 so as not to exceed a predetermined period determined by a T1 recovery time (hereinafter, referred to as T1 simply) of blood to be suppressed by a Beam Sat pulse, determines the application interval 412 so as to suppress blood flowing into an imaging region continuously (desirably in a continuous manner without interruption), and determines the amplitude 414 so as not to exceed a limitation by SAR (Specific Absorption Rate) as well as determines the pulse width 415 according to the determined amplitude 414 while maintaining an application area of the Beam Sat pulse (two-dimensional selective high-frequency pulse).

Additionally, when the number of application times 413 is set, the total application time 411 and the application interval 412 are obtained using the number of application times 413 and the other set application conditions, and then the above application condition determination process is performed.

In order to achieve this, the application condition determination part 142 of the present embodiment performs the three determination process: (i) the total application time determination process for determining whether or not the total application time 411 has a length in which blood in a desired range can be suppressed and is sufficiently shorter compared to the recovery time T1 of longitudinal magnetization components of blood; (ii) the application interval determination process for determining whether or not the application interval 412 is an interval that can be suppressed continuously without interruption; and (iii) the SAR determination process for determining whether or not the application conditions satisfy the SAR regulations that is an absorption amount of an RF pulse per unit time and unit mass.

First, the total application time determination process will be described. When setting the total application time 411 as $T_{all}$ [sec], a suppressible blood vessel length L [cm] is determined by a total application time as $T_{all}$ and a blood flow velocity V [cm/sec]. In a range where the T1 recovery can be ignored, the relationship of these is expressed in the following formula (1).

$$L = V \times T_{all} \quad (1)$$

Figure 5:
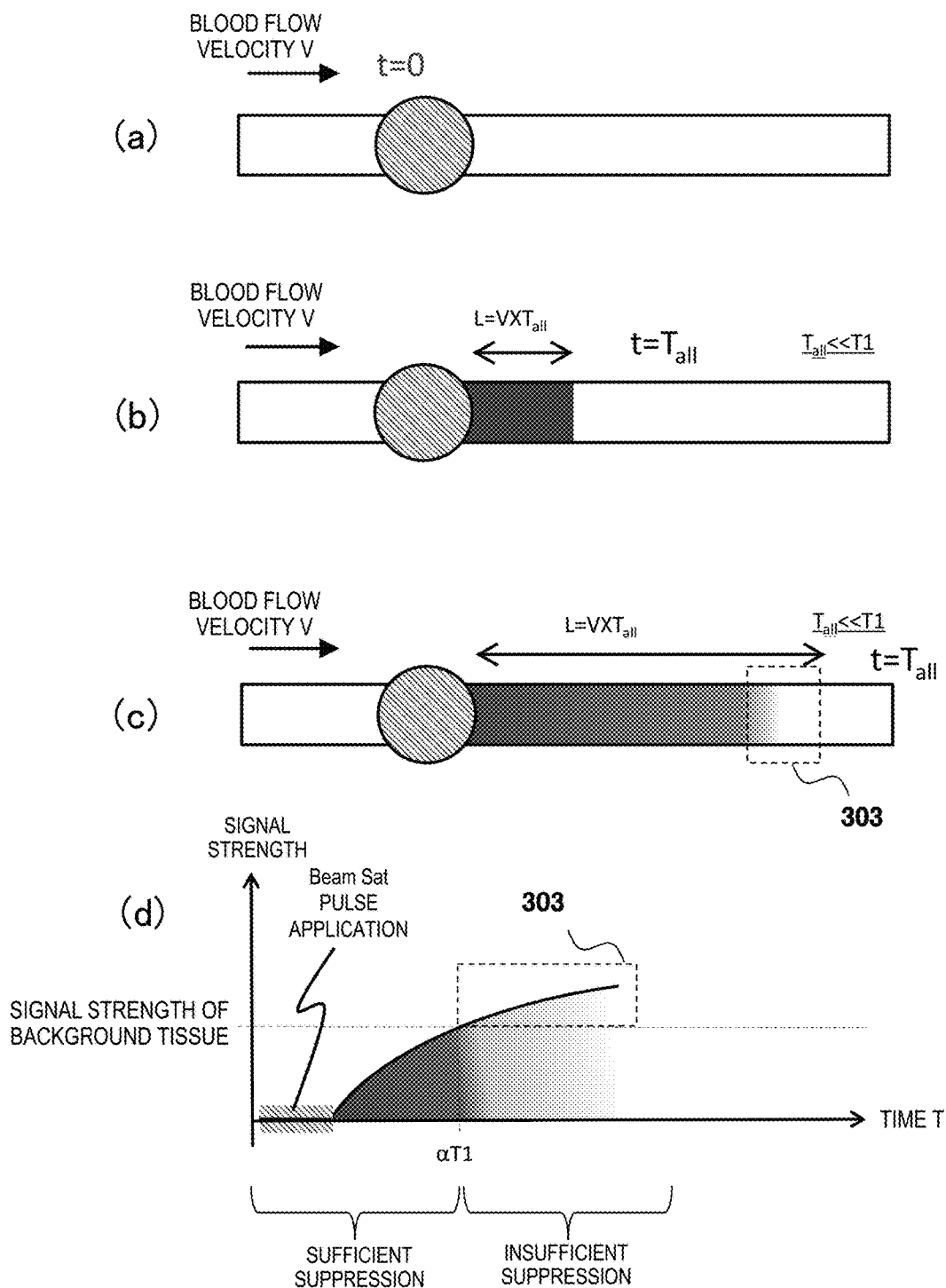
FIGS. 5(a) to 5(d) are explanatory diagrams for explaining a relationship between a Beam Sat pulse, a suppressed blood flow, and T1.

As shown in FIG. 5(a), the Beam Sat pulse 422 is applied in the application position 301, and the suppressed blood proceeds by L during a total application time $T_{all}$ as shown in FIG. 5(b). Therefore, in case of a short total application time $T_{all}$, a suppressible blood vessel length L becomes too short to obtain a sufficient suppression effect. Therefore, the application condition determination part 142 of the present embodiment compares a total application time $T_{all}$ input by an operator with a predetermined first threshold value and sets the total application time $T_{all}$ as the said first threshold value in case of equal to or less than the first threshold value. The first threshold value is determined in advance so as to be suppressible by a desired distance L.

Also, in a case where T1 of blood is longer compared to a total application time $T_{all}$ ($T_{all}$<T1), the suppressed blood reaches a distance L as is. However, in a case where the T1 recovery cannot be ignored, that is, in a case where a total application time $T_{all}$ is considerably longer compared to T1, the T1 recovery is performed until blood suppressed in the Beam Sat pulse application position 301 reaches the periphery 302 as shown in FIGS. 5(c) and 5(d). Therefore, the region 303 that is insufficiently suppressed is generated. Therefore, the application condition determination part 142 of the present embodiment compares a total application time $T_{all}$ input by an operator with a predetermined second threshold value and sets the total application time $T_{all}$ as the said second threshold value in case of more than the second threshold value. The second threshold value is determined in advance in a range where the total application time $T_{all}$ is not affected by the T1 recovery.

In the present embodiment, a blood flow velocity V and a T1 value of an anatomical imaging site are kept in advance. Additionally, a value measured by the Phase Contrast method or the like in advance may be used for the blood flow velocity V. Then, the application condition determination part 142 acquires a T1 value of the said site from imaging site information input as an imaging condition by an operator and calculates the above first and second threshold values using the T1 value to determine whether or not to apply a total application time $T_{all}$ input by the operator. The first threshold value is expressed as $\beta T1$ for which the T1 value is multiplied by a coefficient $\beta$. Also, the second threshold value is expressed as $\alpha T1$ for which the T1 value is multiplied by a coefficient $\alpha$. Here, these coefficients are $0<\beta<\alpha$ and $\beta<=1$. Therefore, the application condition determination part 142 determines whether or not the total application time $T_{all}$ is in a range where it is larger than $\beta T1$ and equal to or less than $\alpha T1$.

Additionally, it may be configured so as to output a message for attracting attention to a user in a case where the total application time $T_{all}$ is out of the above range. Further, in this case, the total application time 411 is not automatically set to $\beta T1$ or $\alpha T1$ again as described above, but a suggestion that a total application time $T_{all}$ is extended or shortened is presented to a user, and it may be configured so as to set it again through the application position reception screen. Also, $\alpha T1$ may be set as a maximum value of T1 that can be input.

Next, the application interval determination process will be described. In a blood vessel range to be suppressed by one application of the Beam Sat pulse 422, the time required for blood in the highest flow to reach the lowest flow (moving time) is determined by an application width (suppression width) $\varphi$ [cm] of the Beam Sat pulse 422 and a blood flow velocity V. Therefore, as shown in the following formula (2), in a case where the application interval 412 $T_{itv}$ is longer than a moving time for which a suppression width $\varphi$ of the Beam Sat pulse 422 was divided by a blood flow velocity, blood that is not suppressed by the Beam Sat pulse 422 is generated. If such blood flows into an imaging region, a suppression rate is reduced. Additionally, φ is the diameter of the Beam Sat pulse 422.

$$T_{itv} > \varphi/V \quad (2)$$

The application condition determination part 142 of the present embodiment determines the application interval 412 set by a user as the application interval 412 used for imaging in a case where the application interval $T_{itv}$ set by the user does not satisfy the formula (2). On the other hand, in a case where the application interval $T_{itv}$ is long, the calculated moving time is set as the application interval 412 used for imaging.

Next, the SAR determination process will be described. When an RF pulse is continuously irradiated, an SAR problem is generated. If an SAR of the Beam Sat pulse 422 according to the application condition set by a user exceeds a regulated value, the application condition of the Beam Sat pulse 422 needs to be changed to reduce the SAR.

The SAR is an absorption amount of an RF pulse per unit time and unit mass and can be reduced by extending the application interval 412 of the Beam Sat pulse 422. Also, the SAR is determined by the amplitude 414 and the pulse width 415 of the RF pulse and can be reduced by suppressing the amplitude 414 of the Beam Sat pulse.

In the present embodiment, because the application interval 412 affects a suppression rate as described above, it is desirable not to change the application interval 412 after determining using the above method. Therefore, the application interval is fixed, and the amplitude 414, which reduces an SAR. That is, the application condition determination part 142 of the present embodiment reduces the amplitude 414 of the Beam Sat pulse 422 so that an SAR calculated under the application conditions set by a user is within a regulated range in case of exceeding the regulated value. At the same time, the pulse width 415 is extended so as to keep an application area [ρT*sec] of the Beam Sat pulse 422 constant.

An SAR is proportional to the square of the amplitude 414 and the pulse width 415. Therefore, for example, when the amplitude 414 is reduced to 1/k of the original, the pulse width 415 is extended to k² times of the original.

Additionally, when an RF pulse amplitude is small, more advanced control is required for the hardware.

According to the hardware, the lowest RF pulse amplitude that can be controlled is determined in advance. In a case where the minimum value of the controllable RF pulse amplitude is stored in the storage unit 123 to reduce the amplitude 414, the calculated amplitude 414 is compared with the minimum value, and in a case where the calculated amplitude 414 is less than the minimum value, it may be configured so as to notify a user of the case.

Figure 6:
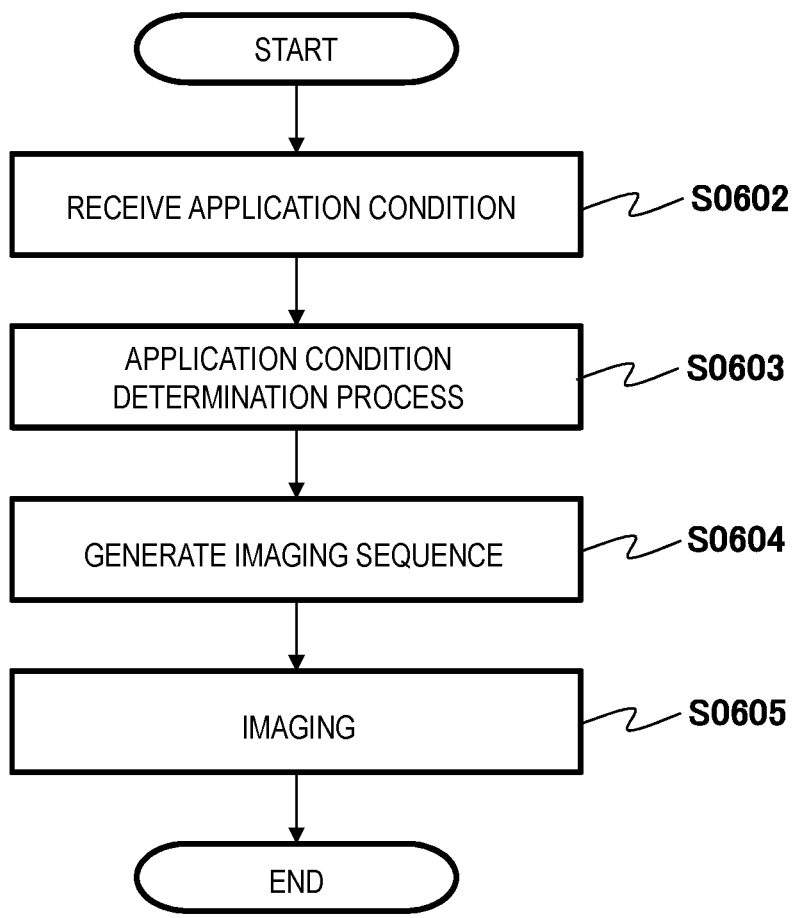
FIG. 6 is a flow chart of the imaging process of the first embodiment.

Next, the imaging process flow by the control unit 120 of the present embodiment will be described. FIG. 6 is a process flow of the imaging process of the present embodiment. The imaging process of the present embodiment starts after a command from a user. Hereinafter, a case of respiration synchronized imaging will be described as an example.

The imaging section 130 obtains a positioning image (Step S0601, not shown in the diagram). A pulse sequence and imaging parameters when imaging the positioning image are set in advance. In the present embodiment, for example, the hemodynamics of the portal vein of the liver is observed. Therefore, for example, a positioning image in which the entire liver was imaged is obtained here.

Next, the reception part 141 generates an application position reception screen for determining the position 301 where the Beam Sat pulse 422 is applied and an imaging condition reception screen including an application condition setting window for setting application conditions, and then displays them on the display unit 121. Then, the application position 301 and the application conditions are received through these screens (Step S0602). The application conditions are any two of the total application time 411, the application interval 412, and the number of application times 413 of Beam Sat pulses as well as the amplitude 414 and the pulse width 415 as described above.

The application condition determination part 142 performs the above respective determination processes and performs an application condition determination process for determining application conditions (Step S0603).

The imaging sequence generation section 140 reflects the determined application conditions to generate an imaging sequence (Step S0604). Then, the imaging section 130 executes imaging (Step S0605) according to the generated imaging sequence and ends the process.

Figure 7:
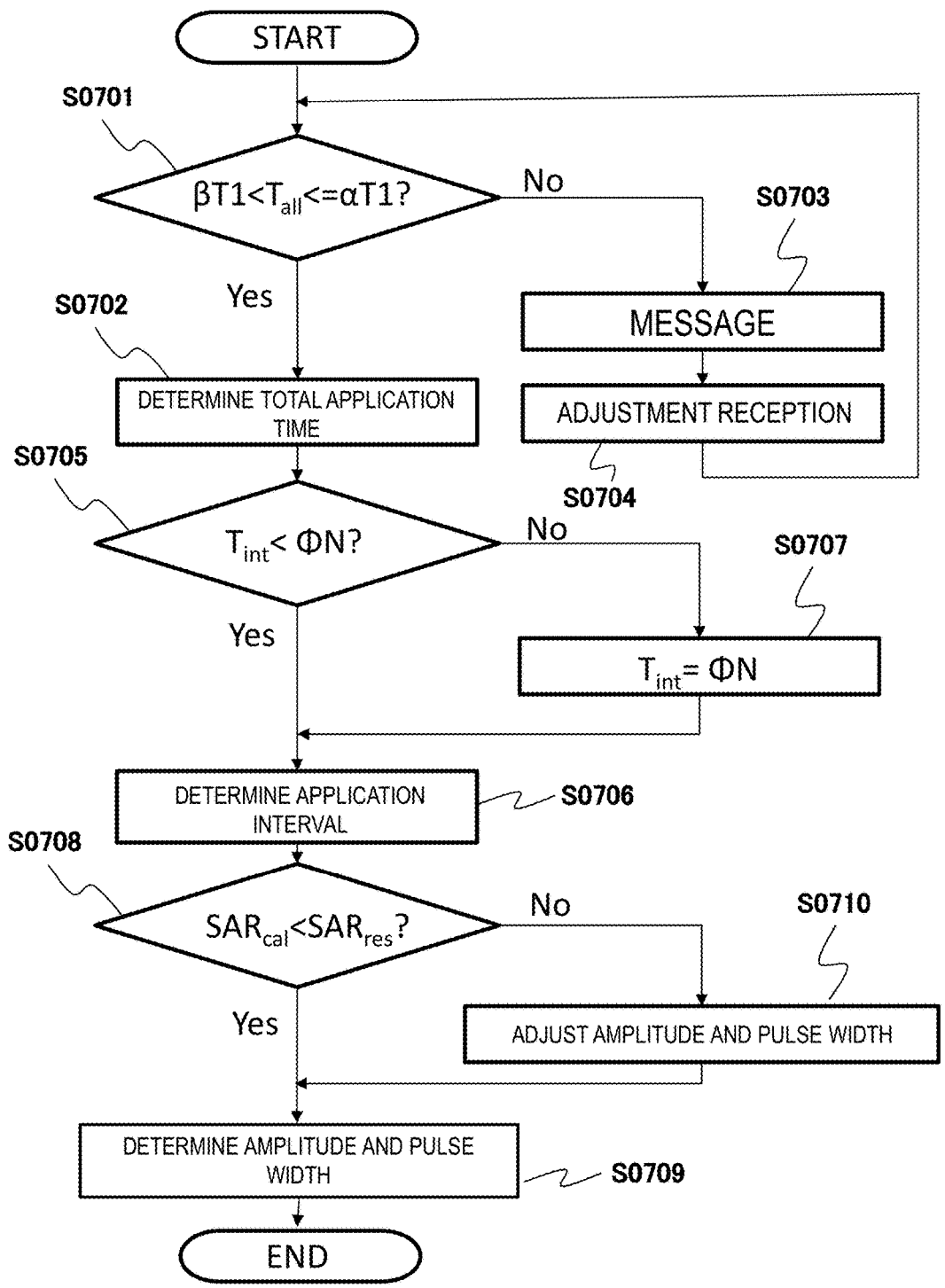
FIG. 7 is a flow chart of the application condition determination process of the first embodiment.

Next, the application condition determination process flow of the present embodiment will be described. FIG. 7 shows a process flow of the application condition determination process.

The application condition determination part 142 first performs a total application time determination process. Here, whether or not a total application time $T_{all}$ is within a range determined by βT1 and αT1 (Step S0701). Then, when it is within the range, the set total application time is determined as a total application time used for imaging (Step S0702). On the other hand, when it is out of the range, a message is displayed to a user (Step S0703), and then the reception part 141 receives an adjustment input (Step S0704). Then, the procedure goes back to Step S0701 to perform the determination again.

Additionally, when a total application time is out of the range, the total application time used for imaging may be automatically determined as βT1 or αT1 as described above.

Next, the application condition determination part 142 performs an application interval determination process. Here, whether or not an application interval $T_{itv}$ is that can suppress blood without interruption is determined (Step S0705).

When the application interval can suppress blood, the set application interval $T_{itv}$ is determined as an application interval used for imaging (Step S0706). On the other hand, when the application interval cannot suppress blood, the application condition determination part 142 calculates an application width φ/a blood flow velocity V (Step S0707) and then determines it as an application interval used for imaging (Step S0706).

Next, the application condition determination part 142 performs an SAR determination process. Here, whether or not an SAR value ($SAR_{cal}$) by application conditions determined so far satisfies a regulated value of SAR ($SAR_{res}$) is determined (Step S0708). When the regulated value is satisfied, the set amplitude and pulse width are determined as those used for imaging (Step S0709). On the other hand, when the regulated value is not satisfied, it is adjusted so as to reduce the amplitude and expand the pulse width by the reduced amount (Step S0710), and the results are determined as the amplitude and the pulse width used for imaging (Step S0709).

Additionally, in the above application condition determination process, either of the total application time determination process or the application interval determination process may be performed first Also, each function of the control unit 120 is achieved, for example, by loading a program previously stored in the storage unit 123 to the memory by the CPU and executing the program.

As described above, the MRI apparatus 100 of the present embodiment is provided with the imaging sequence generation section 140 that applies imaging conditions to a predetermined pulse sequence to generate an imaging sequence and the imaging section 130 that collects echo signals from an imaging region according to the imaging sequence to reconstruct an image from the said echo signals, the pulse sequence includes an IR (Inversion Recovery) pulse and a plurality of the two-dimensional selective high-frequency pulses 422, the imaging conditions include application conditions of the two-dimensional selective high-frequency pulses, the imaging sequence generation section 140 includes the application condition determination part 142 that determines a suitability of the set application conditions and determines application conditions used for the imaging sequence (applied application conditions) according to the determination result, and the application condition determination part 142 determines the applied application conditions so as to suppress the echo signals from blood in a desired blood vessel within SAR (Specific Absorption Rate) limitation.

The application conditions are the total application time 411 and the application interval 412 of the plurality of the two-dimensional selective high-frequency pulses 422 as well as the amplitude 414 and the pulse width 415 of the respective two-dimensional selective high-frequency pulses 422, and then the application condition determination part 142 suppresses blood in a desired range as well as determines the said total application time 411 so as not to exceed a predetermined period determined by a T1 recovery time of the blood, determines the application interval 412 so as to suppress blood flowing into the imaging region continuously without interruption, and determines the amplitude 414 so as not to exceed the limitation by SAR as well as determines the pulse width 415 according to the determined amplitude 414 while maintaining an application area of the two-dimensional selective high-frequency pulse 422.

Thus, according to the present embodiment, when combining the blood vessel visualization method using an IR pulse with a Beam Sat pulse, application conditions of a plurality of Beam Sat pulses are determined so as to equally suppress a signal of blood flowing into a desired imaging region from a desired blood vessel before imaging. Therefore, regardless of a flow velocity of a blood vessel to be imaged, blood in the section lower than an application position of a Beam Sat pulse can be suppressed efficiently, which can surely suppress blood flowing into a desired imaging region from a desired blood vessel to visualize the blood.

Second Embodiment

The second embodiment of the present invention will be described. The present embodiment considers body motion displacement of a blood vessel to be imaged. Hereinafter, an example of a case where body motion to be synchronized is assumed to be respiratory motion will be described in the present embodiment.

Figure 8:
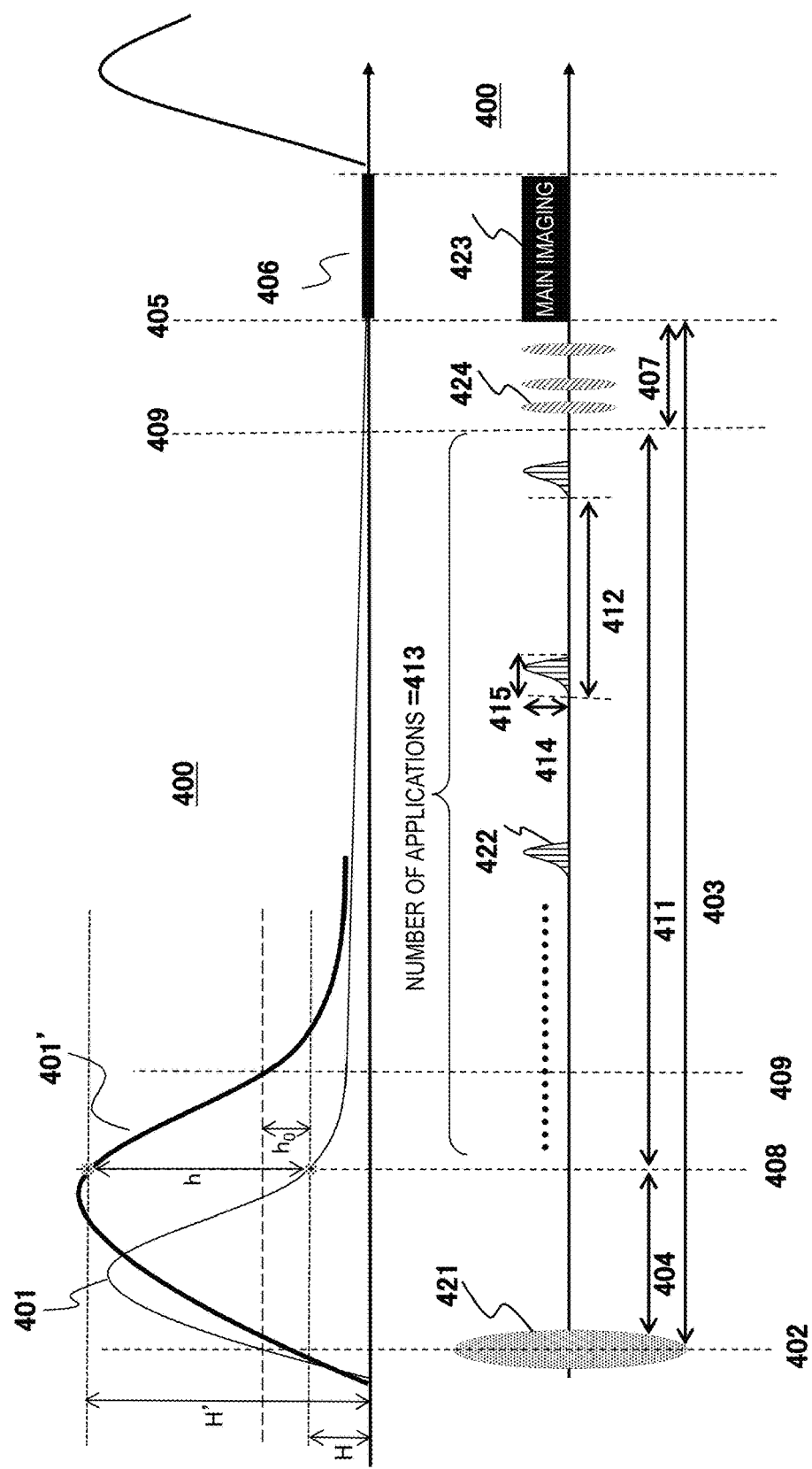
FIG. 8 is an explanatory diagram for explaining an example of the pulse sequence of the second embodiment.

For example, when imaging is performed by synchronizing with respiratory motion of the object 101, there is a case where the respiratory cycle (respiratory waveform) 401 becomes as long as 401' as shown in FIG. 8. When a blood vessel to be suppressed is displaced according to respiratory motion, there is a case of generating suppression failure in which an irradiation position of the Beam Sat pulse 422 deviates from a blood vessel to be irradiated during the total application time 411. There is also a case where an unintended blood vessel and tissue are suppressed, which can cause examination failure. In order to avoid the failure, echo signals obtained in main imaging are sorted according to the application start timing 408 of the respiratory waveform 401 and the Beam Sat pulse 422 in the present embodiment.

Figure 9:
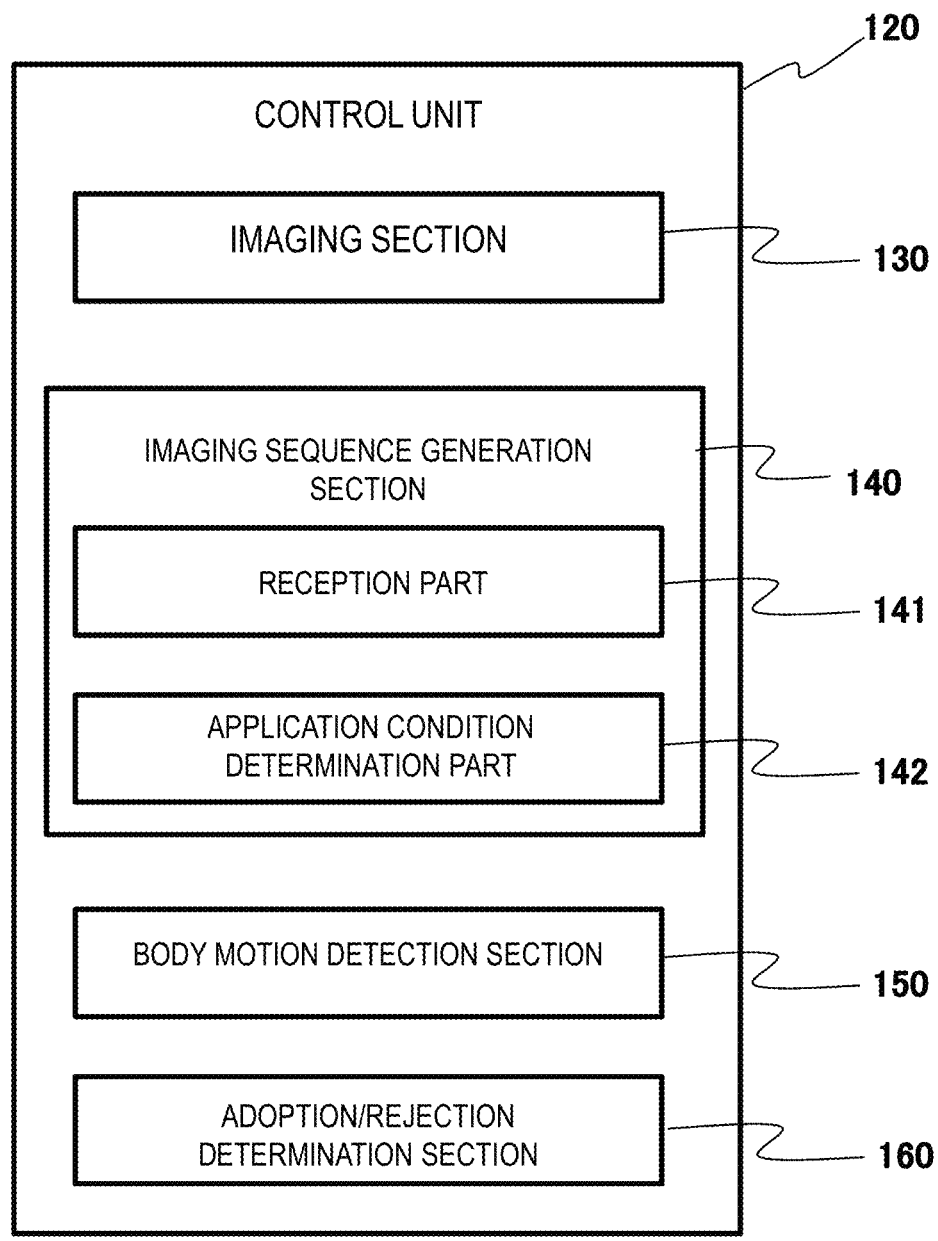
FIG. 9 is a functional block diagram of the control unit of the second embodiment.

The MRI apparatus of the present embodiment basically has a similar configuration to the MRI apparatus 100 of the first embodiment. However, in the present embodiment, the body motion displacement of a blood vessel to be imaged is considered to sort echo signals as described above. Therefore, as shown in FIG. 9, further provided are the body motion detection section 150 that detects a displacement amount by periodic body motion of an object after the peak and the adoption/rejection determination section 160 that determines the adoption or rejection of the echo signals collected by the imaging section 130 according to the relationship between the displace amount and an application start timing of a Beam Sat pulse (two-dimensional selective high-frequency pulse) specified by the application conditions determined by the application condition determination part 142 (applied application conditions). Hereinafter, the configuration different from the first embodiment will be mainly described in the present embodiment.

The body motion detection section 150 of the present embodiment calculates a displacement amount h of a blood vessel to be applied at the Beam Sat pulse application start timing 408 determined by the total application time 411 under application conditions determined by the application condition determination part 142. The displacement amount is calculated based on body motion information from the body motion detection device 124. Additionally, the displacement amount h is, for example, a difference between H' and H of FIG. 8. Here, H is a breathing level of the normal respiratory cycle 401 at the Beam Sat pulse application start timing 408, and H' is a breathing level of the respiratory cycle 401' at the Beam Sat pulse application start timing 408.

The adoption/rejection determination section 160 determines whether or not to use echo signals measured by the imaging section 130 for reconstructing an image. In the present embodiment, the adoption or rejection is determined according to a displacement amount h at the application start timing 408 of the Beam Sat pulse detected by the body motion detection section 150. For example, as shown in FIG. 8, when the displacement amount h detected by the body motion detection section 150 is more than a predetermined threshold value $h_0$, a rejection flag that instructs echo signal cancellation is set. Then, when the displacement amount h is equal to or less than a predetermined threshold value $h_0$, the rejection flag is not set, and echo signals obtained in main imaging are adopted.

The imaging section 130 of the present embodiment reconstructs the image only from echo signals determined to be adopted by the adoption/rejection determination section 160. That is, the echo signals are measured as usual according to the main imaging sequence. Then, whether or not there is a rejection flag is determined, and an image is reconstructed from the obtained echo signals only when the rejection flag is not set. When the rejection flag is set, the said echo signals are cancelled and collected again. Additionally, the imaging section 130 releases the rejection flag setting after determining whether or not there is a rejection flag.

Next, the flow of the imaging process by the control unit 120 of the present embodiment will be described. Here, the process after generating an imaging sequence by the imaging sequence generation section 140 is described.

Figure 10:
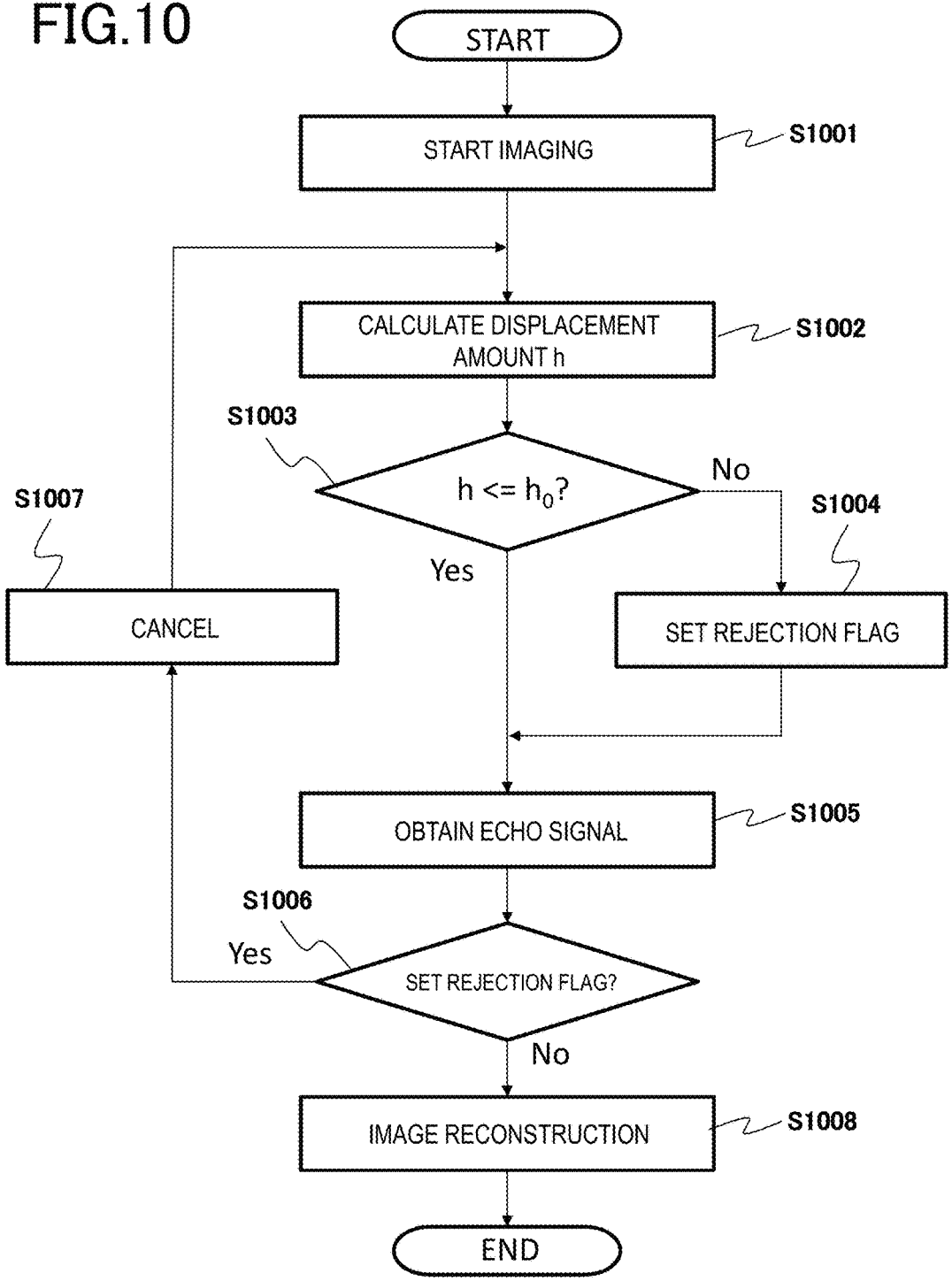
FIG. 10 is a flow chart of the imaging process of the second embodiment.

Hereinafter, an example of a case of respiration synchronized imaging will be described. FIG. 10 is a process flow of the imaging process of the present embodiment. Here, only the process in Step S0604 of the first embodiment is shown. Imaging starts after receiving a start command from a user or after finishing an imaging sequence.

The body motion detection section 150 starts detecting body motion, and the imaging section 130 starts imaging according to the imaging sequence (Step S1001). At this time, the imaging section 130 applies the IR pulse 421 while synchronizing with a respiratory waveform detected by the body motion detection section 150.

The body motion detection section 150 detects a displacement amount h at the Beam Sat pulse application start timing 408 determined by the application condition determination part 142 (Step S1002).

The adoption/rejection determination section 160 compares a detected displacement amount h with a threshold value $h_0$ (Step S1003). Then, when the displacement amount h is larger than the threshold value $h_0$, a rejection flag is set (Step S1004). On the other hand, when the displacement amount h is equal to or less than the threshold value $h_0$, the rejection flag is not set.

The imaging section 130 obtains an echo signal (Step S1005) and then determines whether or not a rejection flag is set before reconstructing an image (Step S1006), and when it is set, the said echo signal is cancelled (Step S1007), and then the process goes back to Step S1001 without reconstructing an image. On the other hand, when the rejection flag is not set, an image is reconstructed (Step S1008), and then the process ends.

As described above, the MRI apparatus of the present embodiment is provided with the body motion detection section 150 that detects a displacement amount by periodic body motion of the object 101 after the peak and the adoption/rejection determination section 160 that determines the adoption or rejection of the echo signals collected by the imaging section 130 according to the relationship between the displace amount h and the application start timing 408 of the two-dimensional selective high-frequency pulse 422 specified by the application conditions determined by the application condition determination part 142 in addition to the imaging section 130 and the imaging sequence generation section 140, the imaging sequence is a body motion synchronization sequence, and the imaging section 130 reconstructs the image only from echo signals determined to be adopted by the adoption/rejection determination section 160.

At this time, the adoption/rejection determination section 160 determines the echo signals obtained in the said imaging sequence to be adopted when the displace amount h at the application start timing 408 is equal to or less than a predetermined threshold value $h_0$.

Thus, according to the present embodiment, when a Beam Sat pulse is combined with the blood vessel visualization method using an IR pulse similarly to the first embodiment, applications conditions of a plurality of Beam Sat pulses are determined so as to equally suppress signals of blood flowing into a desired imaging region from a desired blood vessel before imaging. Therefore, the similar effect to the first embodiment can be obtained.

Additionally, according to the present embodiment, echo signals obtained in the main imaging are sorted depending on the breathing level of a Beam Sat pulse application start timing. Therefore, a signal of suppression failure due to respiratory motion is not used for image reconstruction. Therefore, a desired blood flow can be suppressed with a high accuracy and imaged.

Additionally, a breathing instruction device is provided in the present embodiment, and it may be configured so that the breathing instruction device instructs the object 101 about a breath timing. The instruction is performed by, for example, specifying a timing of exhalation and inhalation so that a displacement amount at the Beam Sat pulse application start timing 408 is equal to or less than a threshold value. The instruction is performed using a voice, a monitor, stimulation by a stimulation device, or the like.

Figure 11:
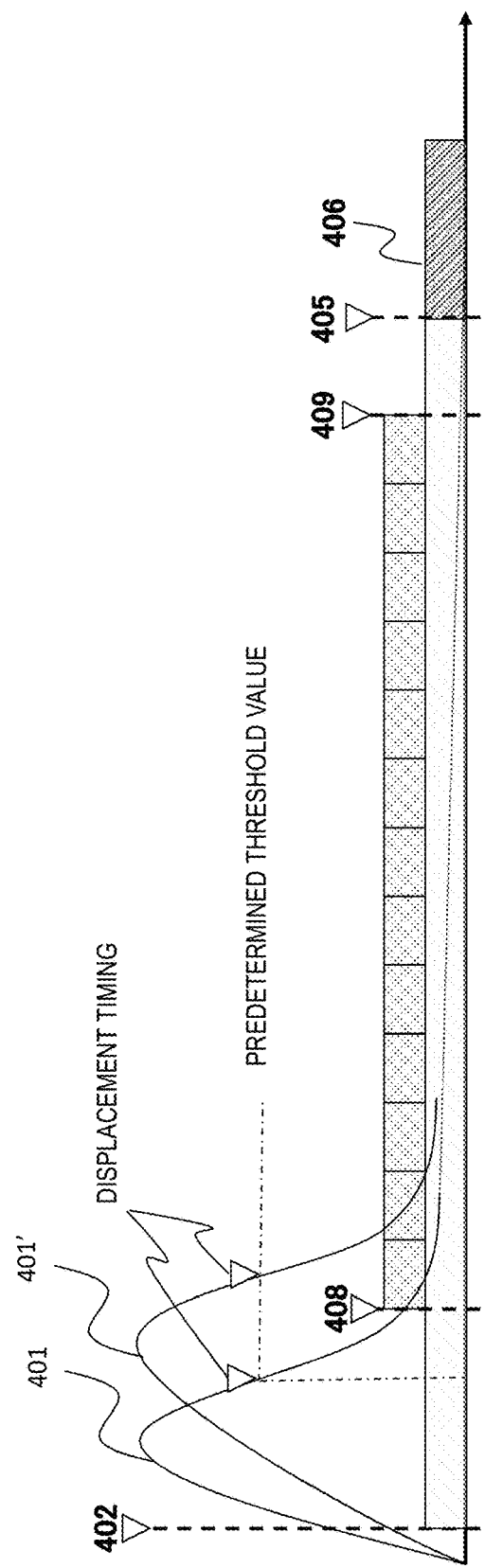
FIG. 11 is an explanatory diagram for explaining the breathing instruction display of the second embodiment.

When instructing using a monitor, an example screen to be displayed to a user is shown in FIG. 11. As shown in the present diagram, a summary of the application timings (411 and 412) of Beam Sat pulses determined by the application condition determination part 142 and the execution period 406 of the main imaging 423 is displayed along with the respiratory waveform 401, and the user is prompted to breath so that a displacement timing does not exceed the Beam Sat pulse application start timing 408. Here, as a summary, the application timing 402 of the IR pulse 421, the application start timing 408 of the Beam Sat pulse 422, the application end timing 409, the main imaging start timing 405, and the main imaging execution period 406 are shown for example.

Third Embodiment

The third embodiment of the present invention will be described. The present embodiment considers body motion displacement of a blood vessel to be imaged similarly to the second embodiment. In the present embodiment, the displacement of a blood vessel to be imaged is considered, application conditions of the Beam Sat pulse 422 are changed, and then cancellation of echo signals accordingly obtained is determined.

The MRI apparatus of the present embodiment basically has a similar configuration to the second embodiment. However, the processes of the body motion detection section 150, the adoption/rejection determination section 160, and the imaging section 130 are different in the present embodiment because displacement is considered to determine application conditions. Hereinafter, the processes different from the second embodiment will be mainly described in the present embodiment.

The body motion detection section 150 of the present embodiment monitors respiratory motion and notifies the application condition determination part 142 of a displacement amount at a predetermined time interval.

The imaging section 130 starts applying the Beam Sat pulse 422 at a later timing of the application start timing (setting timing) 408 of the Beam Sat pulse 422 specified by the application condition determination part 142 and a time equal to or less than a threshold value predetermined by a displacement amount (displacement timing). That is, when the setting timing 408 is earlier than the displacement timing, the application of the Beam Sat pulse 422 starts from the displacement timing instead of the setting timing 408.

The adoption/rejection determination section 160 compares a displacement timing with the setting timing 408 and determines echo signals obtained in the said imaging sequence (main imaging immediately after this) to be adopted when the setting timing 408 is the displacement timing or later and when the setting timing 408 is earlier than the displacement timing and a period from the displacement timing to the application end timing 409 of the two-dimensional selective high-frequency pulse specified by application conditions determined by the application condition determination part 142 is longer than a predetermined period. In the other cases, cancellation is determined, and then a cancellation frag is set.

Additionally, the adoption/rejection determination section 160 calculates a length L of a blood vessel to be suppressed during a total application time specified a time $T_{all2}$ from a displacement timing to the application end timing 409 using the formula (1) when the setting timing 408 is earlier than the displacement timing. Then, whether or not the length is long enough to suppress a desired range is determined, and in case of enough length, echo signals obtained in the said imaging sequence (main imaging immediately after this) are determined to be adopted.

Additionally, the determination is performed by comparing a calculated time $T_{all2}$ with a threshold value $\beta T1$ set in the first embodiment. In a case where $\beta T1 < T_{all2}$ is satisfied, the adoption is determined.

Next, the flow of the imaging process by the control unit 120 of the present embodiment will be described. Here, the process after an imaging sequence is generated by the imaging sequence generation section 140 is described.

Figure 12:
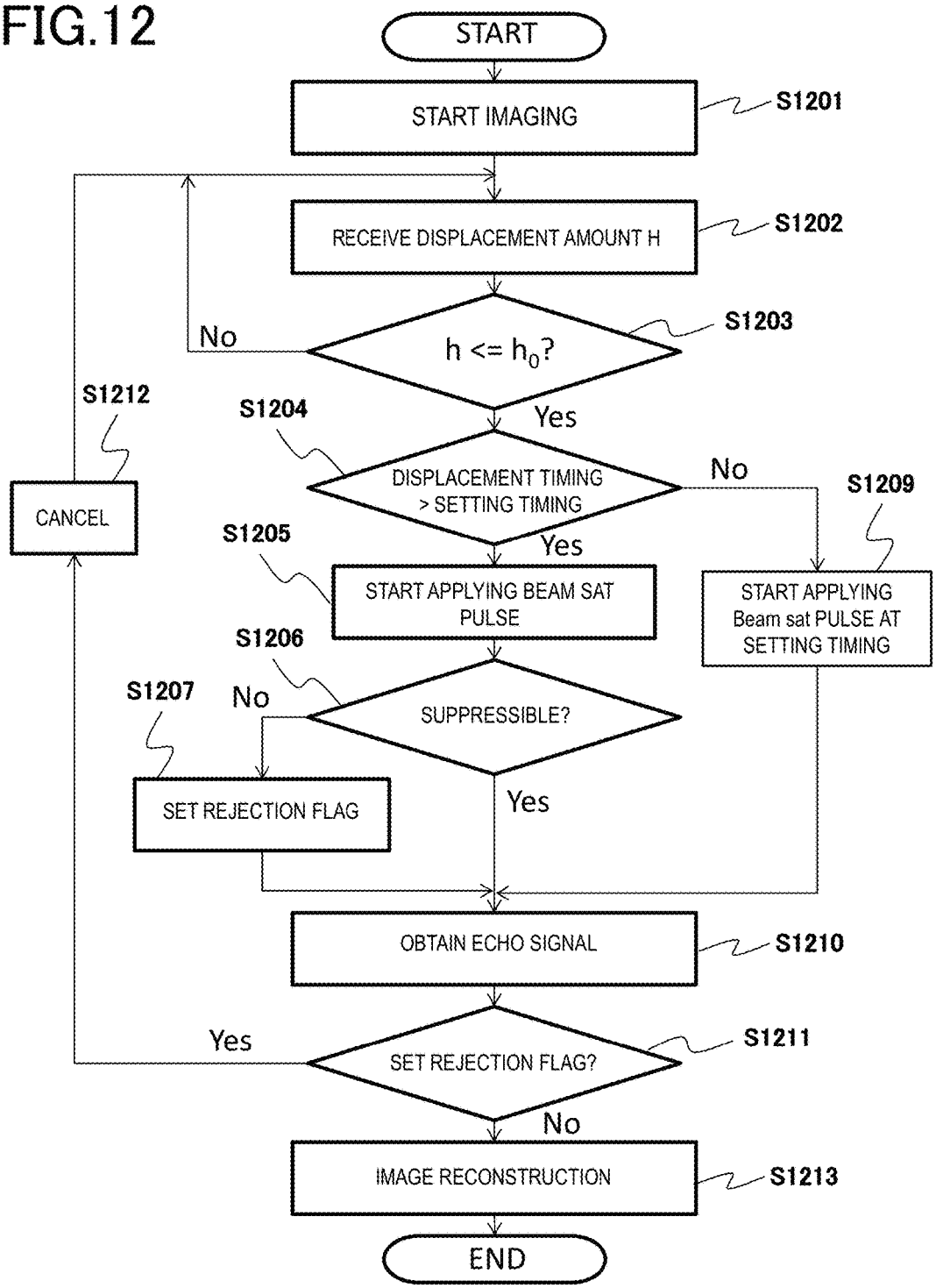
FIG. 12 is a flow chart of the imaging process of the third embodiment.

Hereinafter, a case of respiration synchronized imaging will be described as an example. FIG. 12 is a processing flow of the imaging process of the present embodiment. Here, only the process in Step S0604 of the first embodiment is shown. Imaging starts after receiving a start command form a user or after finishing an imaging sequence.

The body motion detection section 150 starts detecting body motion, and the imaging section 130 starts imaging according to the imaging sequence (Step S1201). At this time, the imaging section 130 applies the IR pulse 421 according to the respiratory waveform detected by the body motion detection section 150.

Then, the imaging section 130 receives a displacement amount h at a predetermined time interval from the body motion detection section 150 (Step S1202). Waiting for the received displacement amount h becomes equal to or less than a threshold value $h_0$ after the amount exceeds the maximum value (Step S1203) is performed. The time when receiving the displacement amount h that became equal to or less than the threshold value $h_0$ is set as a displacement timing, and it is compared to a setting timing (Step S1204).

When a displacement timing (displacement T) is a setting timing (setting T) or later, Beam Sat pulse application starts immediately (Step S1205). At this time, the adoption/rejection determination section 160 specifies a total application time from this displacement timing and determines whether or not desired blood can be suppressed sufficiently by the total application time ($\beta T1 < T_{all2}$) (Step S1206).

Then, if impossible, a rejection flag is set (Step S1207). On the other hand, if possible, a rejection flag is not set.

On the other hand, when a displacement timing is before a setting timing, the imaging section 130 starts application of the Beam Sat pulse 422 at the setting timing (Step S1209).

The imaging section 130 starts main imaging after applying a Beam Sat pulse and the other predetermined pre-pulse and obtains an echo signal (Step S1210). Then, whether or not a rejection flag is set is determined (Step S1211), and if the rejection flag is set, the said echo signal is cancelled (Step S1212), and then the process goes back to Step S1202 without reconstructing an image. On the other hand, if the rejection flag is not set, an image is reconstructed (Step S1213), and then the process ends.

Additionally, when it is determined that a length of the total application time 411 is insufficient in Step S1206, it may be configured so that a signal is not cancelled but Beam Sat pulse application itself is cancelled for the one cycle.

As described above, the MRI apparatus of the present embodiment is provided with the above imaging section 130, the imaging sequence generation section 140, the body motion detection section 150, and the adoption/rejection determination section 160 compares a displacement timing at which the displacement amount h becomes a predetermined threshold value H with the application start timing 408 and determines echo signals obtained in the said imaging sequence to be adopted when the application start timing 408 is after the displacement timing and when the application start timing 408 is earlier than the displacement timing and a period from the displacement timing to the application end timing 409 of the two-dimensional selective high-frequency pulse 422 specified by application conditions determined by the application condition determination part 142 is longer than a predetermined period, and then the imaging section 130 starts application of the two-dimensional selective high-frequency pulse 422 instead of the application start timing 408 from the displacement timing when the application start timing 408 is earlier than the displacement timing.

Thus, according to the present embodiment, when combining the blood vessel visualizing method using an IR pulse with a Beam Sat pulse similarly to the first embodiment, applications conditions of a plurality of Beam Sat pulses are determined so as to equally suppress signals of blood flowing into a desired imaging region from a desired blood vessel before imaging. Therefore, the similar effect to the first embodiment can be obtained.

Additionally, according to the present embodiment, echo signals obtained in main imaging are sorted depending on the breathing level of a Beam Sat pulse application start timing. Therefore, a signal of suppression failure due to respiratory motion is not used for image reconstruction. Therefore, a desired blood flow can be suppressed with a high accuracy and imaged.

Additionally, a breathing instruction device is provided even in the present embodiment similarly to the second embodiment, and it may be configured so that a breathing timing is instructed to the object 101 by the breathing instruction device.

Fourth Embodiment

Next, the fourth embodiment of the present invention will be described. Although the number of spots to be suppressed by the Beam Sat pulse 422 is one, that is, one blood vessel is suppressed in the first embodiment, multiple spots are suppressed in the present embodiment.

The MRI apparatus of the present embodiment basically has a similar configuration to the MRI apparatus 100 of the first embodiment. However, in the present embodiment, the different are the processes of the imaging sequence generation section 140 and the application condition determination part 142. Hereinafter, the configuration different from the first embodiment will be mainly described in the present embodiment.

The present embodiment, when applying a Beam Sat pulse to multiple spots (multiple blood vessels), blood vessels to which the pulse is applied are changed cyclically to obtain an equivalent suppression effect for the respective applied blood vessels.

That is, a Beam Sat pulse is cyclically applied to a plurality of blood vessels in the present embodiment, and the application condition determination part 142 determines the application interval so that blood flowing from each blood vessel is suppressed respectively in a continuous manner without interruption and considers the two-dimensional selective high-frequency pulse to be applied to all the blood vessels in order to determine the amplitude and the pulse width so as not to exceed a limitation by the SAR.

The detailed description will be made using FIGS. 13(a) and 13(b). In the present embodiment, the number of application spots is shown as M. However, a case of applying Beam Sat pulses to the four spots is shown as an example in FIG. 13(a).

Figure 13:
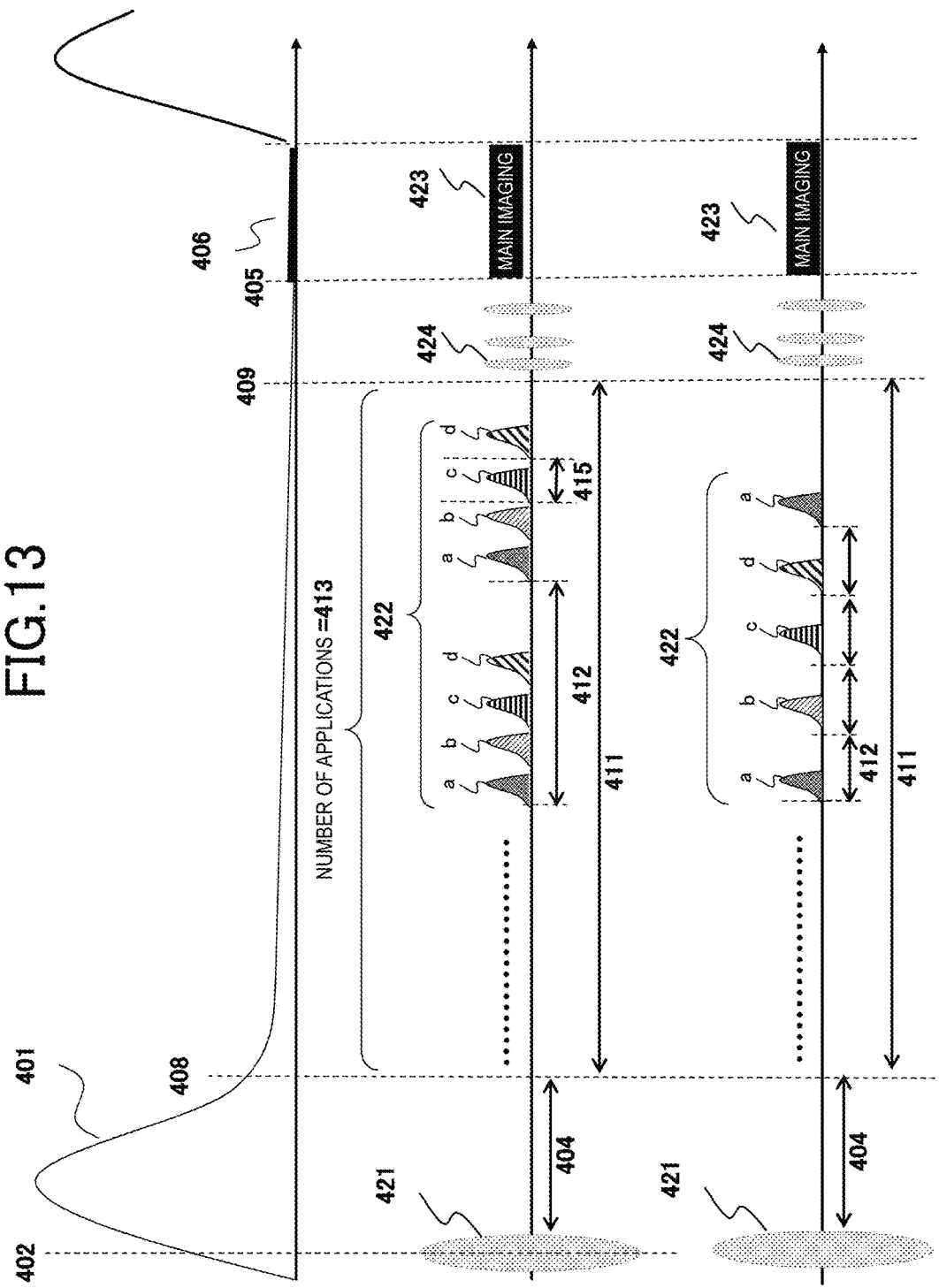
FIG. 13 is an explanatory diagram for explaining an example of the pulse sequence of the fourth embodiment.

For example, when the application interval 412 is sufficiently large compared to the pulse width 415, an application condition is determined so that M pieces of the Beam Sat pulses 422 are applied during the application interval 412 as shown in FIG. 13(a). Additionally, in FIG. 13(a), the four Beam Sat pulses of 422a, 422b, 422c, and 422d are applied.

That is, because Beam Sat pulses are applied at the application interval 412 in M spots of application positions to a blood vessel, the Beam Sat pulses are applied at a time interval of 1/M of the application interval 412 on a pulse sequence.

In this case, the total application time 411 is similar to the first embodiment. Also, the application interval 412 of each application position becomes similar to the first embodiment. However, an application interval does not depend on the application position when determining whether or not to satisfy the SAR limitation, the interval becomes M times of the application interval 412 in the first embodiment.

Therefore, in this case, the application condition determination part 142 performs the total application time determination process and the application interval determination process similarly to the first embodiment. On the other hand, in the SAR determination process, the number of applications per unit time is multiplied M times to determine an SAR.

Additionally, in a case of exceeding a regulated value in the SAR determination process, the amplitude 414 of the respective Beam Sat pulses 422 (422a, 422b, 422c, and 422d) is reduced to extend the pulse width 415 similarly to the first embodiment.

Also, when the application interval 412 is not sufficiently large compared to the pulse width 415, the Beam Sat pulses 422 (422a, 422b, 422c, and 422d in the example of FIG. 13(b)) are cyclically applied to M spots at the respective application intervals 412 as shown in FIG. 13(b).

As shown in the present diagram, the Beam Sat pulses 422 are applied in each application position at an interval of M times of the application interval 412. However, the Beam Sat pulses 422 are applied at the application interval 412 on a pulse sequence.

In this case, the total application time 411 is similar to the first embodiment. Also, the application interval 412 that affects an SAR is similar to the first embodiment. On the other hand, an application interval in each application position becomes M times of the application interval 412.

Therefore, the application condition determination part 142 performs the total application time determination process and the SAR determination process similarly to the first embodiment. On the other hand, in the application interval determination process, the application interval 412 is multiplied M times to determine an interval using the above formula (2).

As described above, the MRI apparatus 100 of the present embodiment is provided with the above imaging section 130 and imaging sequence generation section 140, the two-dimensional selective high-frequency pulse 422 is cyclically applied to a plurality of blood vessels, and the application condition determination part determines the application interval 412 so that blood flowing from each blood vessel is suppressed respectively in a continuous manner without interruption and considers the two-dimensional selective high-frequency pulse 422 to be applied to all the blood vessels in order to determine the amplitude 414 and the pulse width 415 so as not to exceed a limitation by the SAR.

Thus, according to the present embodiment, when a Beam Sat pulse is combined with the blood vessel visualization method using an IR pulse similarly to the first embodiment, applications conditions of a plurality of Beam Sat pulses are determined so as to equally suppress signals of blood flowing into a desired imaging region from a desired blood vessel before imaging. Therefore, the similar effect to the first embodiment can be obtained.

Fifth Embodiment

The fifth embodiment of the present invention will be described. In the present embodiment, blood flow velocity information is further acquired.

The MRI apparatus of the present embodiment basically has a similar configuration to the MRI apparatus 100 of the first embodiment. However, in the present embodiment, blood flow velocity information is acquired. Therefore, as shown in FIG. 14(a), the control unit 120 of the present embodiment is further provided with the flow velocity calculation section 170 that calculates a flow velocity of blood in an imaging region from a reconstructed image.

Also, the imaging sequence of the present embodiment includes a predetermined spare time 407 between an application end timing of a plurality of Beam Sat pulses and a start timing of main imaging. The flow velocity calculation section 170 of the present embodiment calculates the flow velocity using the spare time 407 and a length of an unsuppressed blood flow.

Additionally, the other pre-pulse may be applied during the spare time 407. That is, as shown in FIG. 4 of the first embodiment, a period in which a fat suppression pulse is applied as the pre-pulse 424 may be utilized. This imaging sequence is generated by the imaging sequence generation section 140, and information of the spare time 407 to be set for the imaging sequence is notified to the flow velocity calculation section 170.

A method for acquiring blood flow velocity information by setting the time (spare time) 407 when no Beam Sat pulse is applied immediately before main imaging will be described below.

Figure 15:
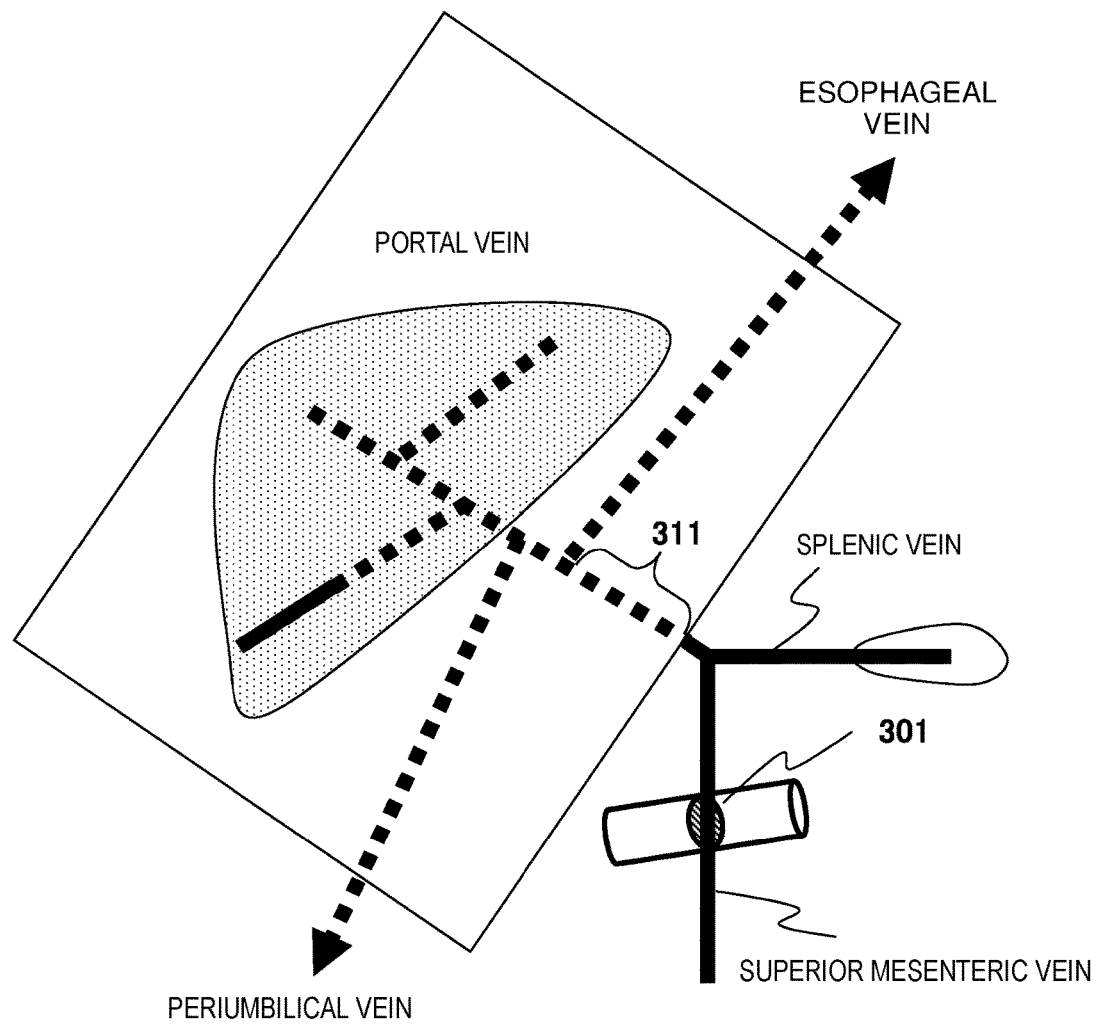
FIG. 15 is an explanatory diagram for explaining the flow velocity calculation principle of the fifth embodiment.

As shown in FIG. 15, because unsuppressed blood flows in by setting the spare time 407, the unsuppressed region 311 appears on the FOV side (peripheral side) from a Beam Sat pulse application position. A length $L_{Nrs}$ [CM] of the unsuppressed region (non-suppression region) 311 is expressed in the following formula (3) using a blood flow velocity V [cm/sec] and the spare time 407 $T_{Nap}$ [sec].

$$L_{Nrs} = V \times T_{Nap} \qquad (3)$$

Therefore, a blood flow velocity V can be calculated from the following formula (4) using the spare time 407 $T_{Nap}$ and a length $L_{Nrs}$ of the non-suppression region 311.

$$V = L_{Nrs} = =/T_{Nap} \qquad (4)$$

Figure 16:
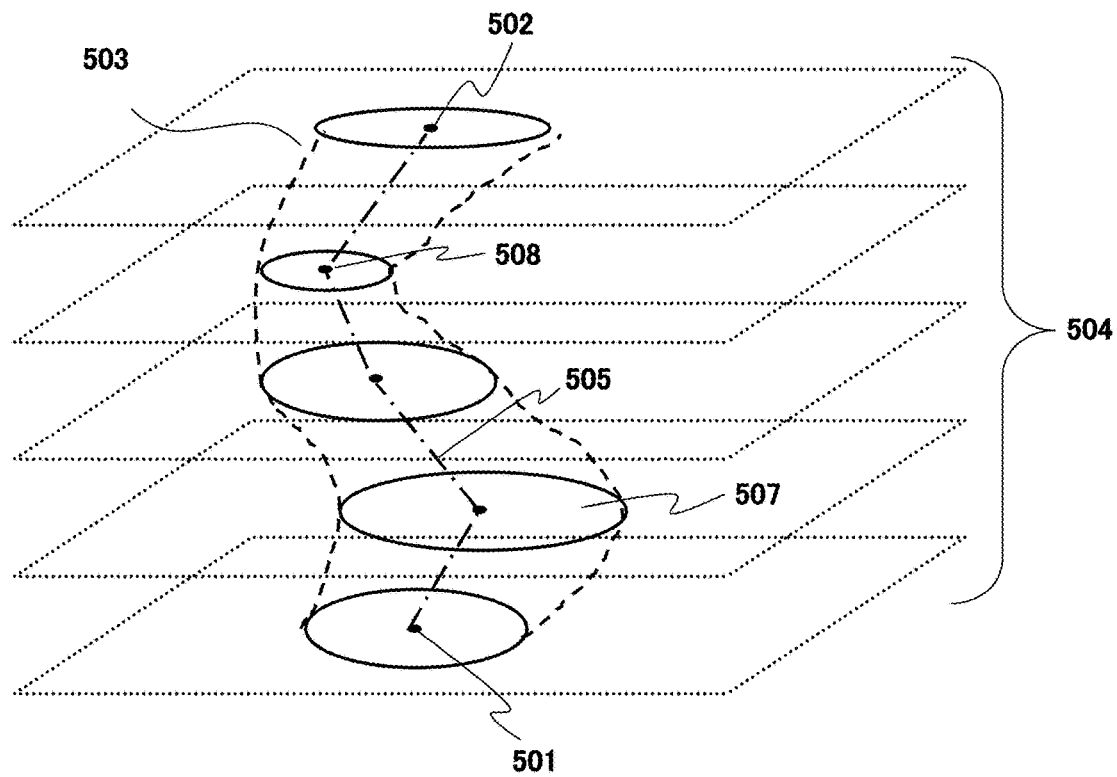
FIG. 16 is an explanatory diagram for explaining the measurement method of a non-suppression region using the flow velocity calculation section of the fifth embodiment.

The flow velocity calculation section 170 uses the spare time 407 $T_{Nap}$ and a length $L_{Nrs}$ of the non-suppression region 311 to calculate a blood flow velocity of an imaging target region (suppression target region). At this time, a value received from the imaging sequence generation section 140 is used as the spare time 407 $L_{Nrs}$. Also, a length $L_{Nrs}$ of the non-suppression region 311 is measured on a reconstructed image. The specific measurement method by the flow velocity calculation section 170 will be described using FIG. 16.

Here, in a case of visualizing a blood vessel by applying the IR pulse 421, a position and a range of a blood vessel in which suppressed blood flows are identified to calculate the length using that the suppressed blood has a higher signal than the background substance.

Setting a pixel of the Beam Sat pulse application position 301 as the starting point 501, region growing is performed for an imaging target site side from the application position 301 to check a pixel value of each pixel (signal value). Setting a pixel in the farthest position from the starting point 501 as the end point 502 in pixels whose pixel values (signal values) are equal to or less than a predetermined threshold value, the blood vessel 503 that was visualized on the periphery side from the application position 301.

Next, by identifying the intersection plane 507 of the blood vessel 503 and n pieces of the flat planes 504 on which the straight line from the starting point 501 to the end point 502 is a normal line, the gravity center 508 of the said intersection plane 507 is calculated. The same process is performed in all the n pieces of the flat planes 504 to calculate the gravity centers 508 of the respective intersection planes 507. Lastly, all the distances 505 between the gravity centers of the intersection planes 507 that are adjacent each other are added to set as the length 311.

Additionally, the intervals between n pieces of flat planes are, for example, the same as a slice thickness of main imaging.

Also, a length $L_{Nrs}$ of the non-suppression region 311 may be measured by an operator on an obtained image.

The flow velocity calculation section 170 calculates a blood flow velocity after imaging by the imaging section 130. Each process flow by the imaging section 130 and the imaging sequence generation section 140 is similar to the first embodiment other than the difference of the above generated imaging sequence.

As described above, the MRI apparatus 100 of the present embodiment is provided with the flow velocity calculation section 170 that calculates a flow velocity of the blood from the image in addition to the above imaging section 130 and imaging sequence generation section 140, the imaging sequence includes a predetermined spare time 407 between the application end timing 409 of the plurality of the two-dimensional selective high-frequency pulses and the start timing 405 of main imaging, and the flow velocity calculation section 170 calculates the flow velocity using the spare time 407 and a length of an unsuppressed blood flow.

Thus, according to the present embodiment, when a Beam Sat pulse is combined with the blood vessel visualization method using an IR pulse similarly to the first embodiment, applications conditions of a plurality of Beam Sat pulses are determined so as to equally suppress signals of blood flowing into a desired imaging region from a desired blood vessel before imaging. Therefore, the similar effect to the first embodiment can be obtained.

Furthermore, according to the present embodiment, blood flow velocity information of a blood vessel to be imaged can also be acquired.

Additionally, although a blood flow velocity is calculated in the present embodiment, it may be configured so as to estimate a range to be suppressed when the blood flow velocity is already known by the previous measurement. In this case, as shown in FIG. 14(b), the control unit 120 is further provided with the suppression range calculation section 180 that calculates a suppression range from a blood flow velocity instead of the flow velocity calculation section 170, and the suppression range calculation section 180 calculates a suppression range from a blood flow velocity and a TI recovery time of the said blood.

Additionally, when R is a radius of the suppression range, the radius R is calculated in the following formula (5).

$$R = V \times \alpha T1 \qquad (5)$$

Figure 17:
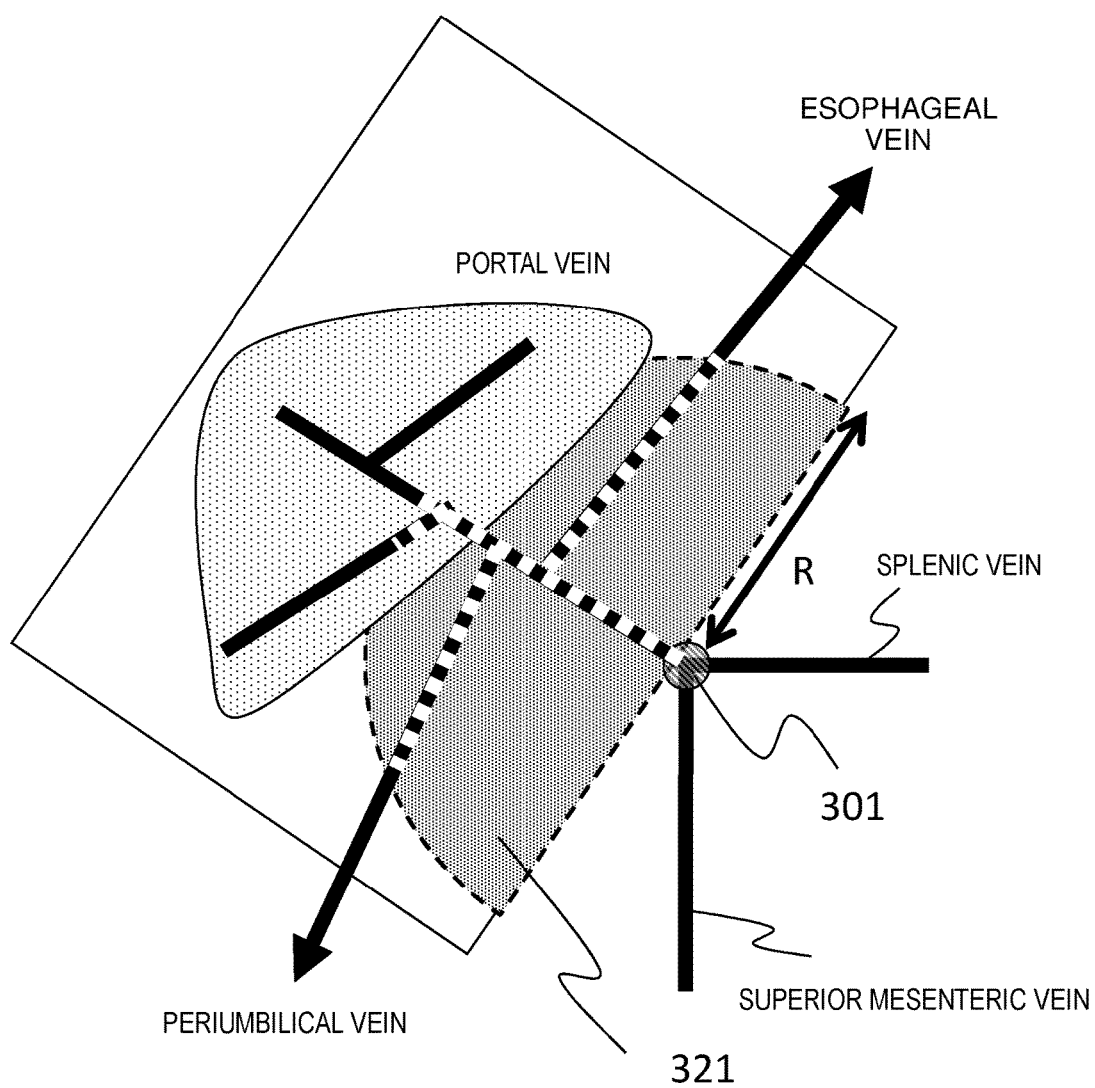
FIG. 17 is an explanatory diagram for explaining a display example of the suppression range of the fifth embodiment.

The suppression range calculation section 180 displays a calculated suppression range on an image obtained by the imaging section 130. FIG. 17 shows a display example. Here, the shown example is a case where the application position 301 of the Beam Sat pulse 422 is set as an intersection of the splenic vein and the superior mesenteric vein. The suppression range calculation section 180 displays the half circle on the downstream side than an application position in the radius R circle where the Beam Sat pulse application position 301 is centered as the suppression range 321 on the obtained image.

Additionally, a blood flow velocity is measured using, for example, the PC method.

Additionally, in the above respective embodiments, although an example of a case of imaging while the body motion is synchronized with respiration whose cycle is relatively long is described, the cyclic body motion to be synchronized is not limited to the respiration. For example, the body motion may be heartbeats.

Figure 18:
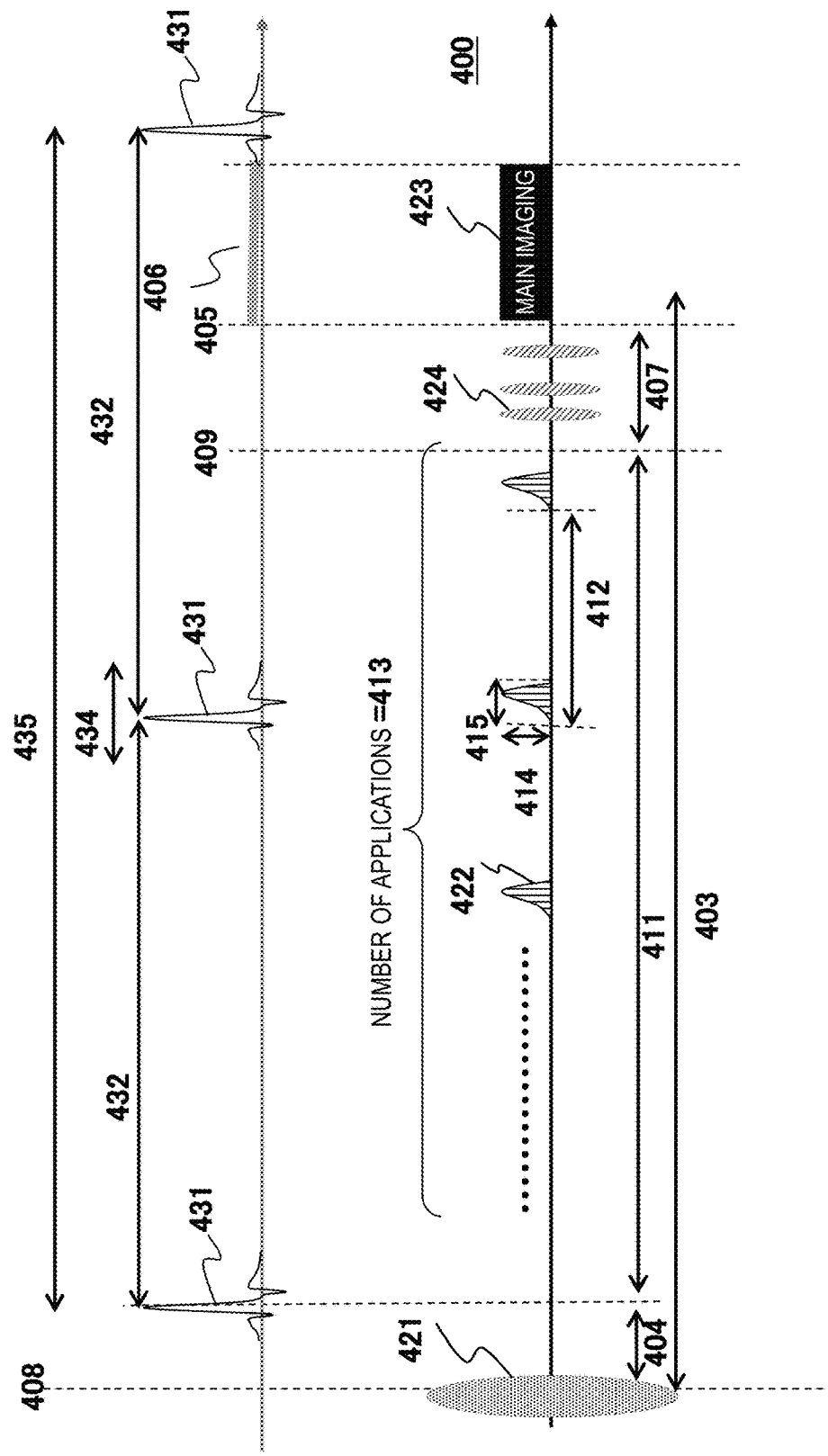
FIG. 18 is an explanatory diagram for explaining a pulse sequence of electrocardiographic synchronization in a variation of the fifth embodiment.

As shown in FIG. 18, the electrocardiographic waveform 431 has a short cycle compared to the respiratory waveform 401. Therefore, in a case of applying the IR pulse 421, applying a plurality of the Beam Sat pulses 422 that can suppress a desired blood vessel, and performing main imaging within the one cardiac cycle 432, there is a high possibility that the total application time 411 of the Beam Sat pulses 422 cannot be sufficiently taken, which results in insufficient suppression. Therefore, when executing the pulse sequence 400 by heartbeat synchronization, a plurality of the cardiac cycles 432 are designed to be executed as the synchronization cycle 435, which obtains a sufficient suppression effect.

Figure 19:
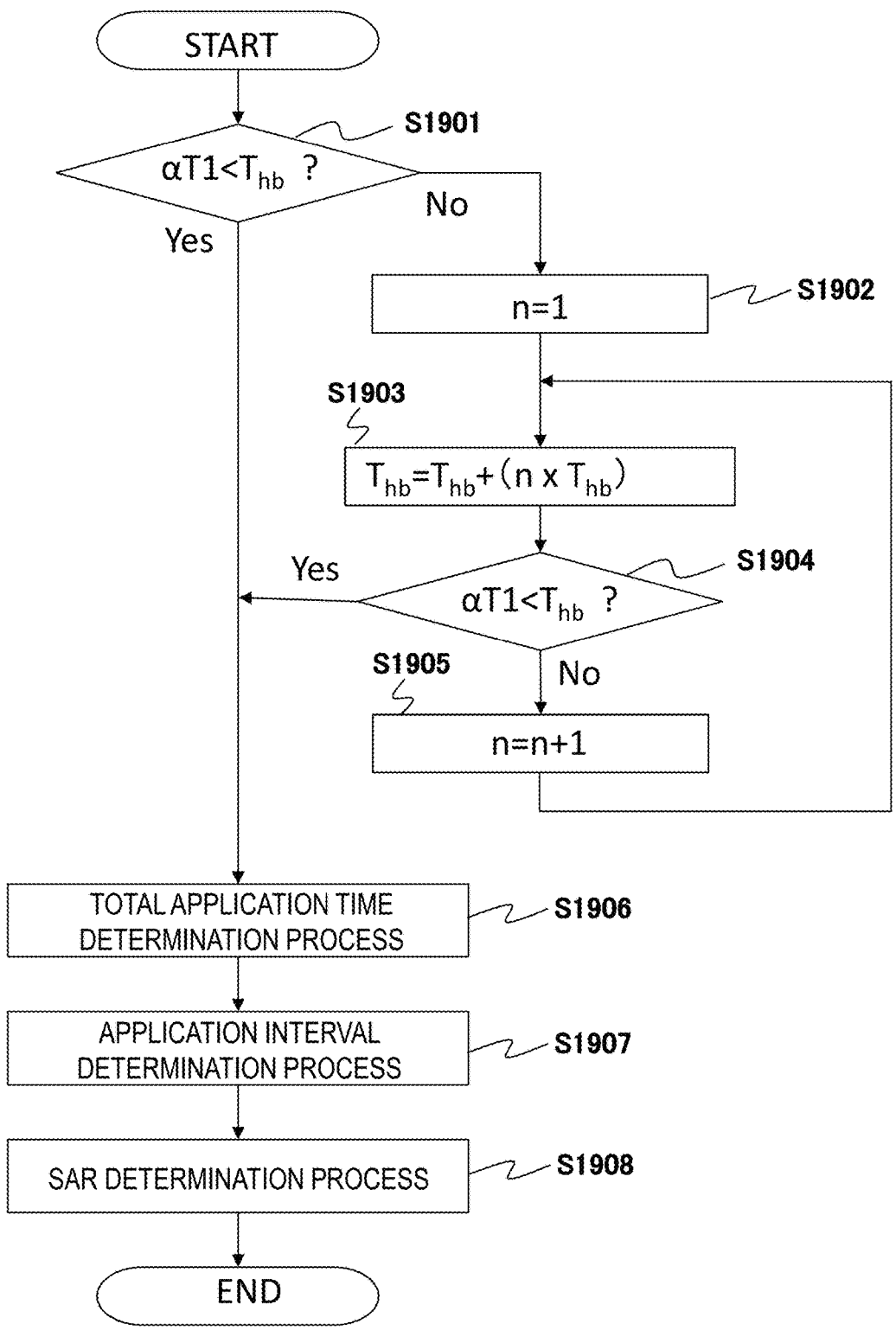
FIG. 19 is a flow chart of the application condition determination process during electrocardiographic synchronization in a variation of the fifth embodiment

Additionally, the imaging process flow in this case is similar to the imaging process of the first embodiment. On the other hand, the application condition determination process flow by the application condition determination part 142 is different. Hereinafter, the application condition determination process flow in case of electrocardiographic synchronization will be described following the process flow of FIG. 19.

First, the synchronization cycle determination process is performed. Here, the maximum cardiac cycle number within $\alpha T1$ is obtained. A cycle by the obtained cardiac cycle number is set as the synchronization cycle 435, and imaging is executed in synchronization with the synchronization cycle 435.

First, a length $T_{hb}$ of the cardiac cycles 432 and αT1 are compared (Step S1901). When αT1 is shorter than the length $T_{hb}$ of the cardiac cycle 432, the process proceeds to the total application time determination process as is.

On the other hand, when αT1 is equal to or longer than the length $T_{hb}$ of the cardiac cycle 432 (αT1>=$T_{hb}$), the number of cardiac cycles 432 is increased until αT1 is shorter than the length of the cardiac cycle 432. Specifically, the counter n is set to 1 (Step S1902), and then a value in which $T_{hb}$ is added to n×$T_{hb}$ is set as a new $T_{hb}$ (Step S1903) to compare with αT1 (Step S1904). Then, n is increased by one increment until αT1<$T_{hb}$ is satisfied (Step S1905), and Steps S1903 and S1904 are repeated. When αT1<$T_{hb}$ is satisfied eventually, a cardiac cycle number at that time is set as the synchronization cycle 435.

After the synchronization cycle 435 is determined, the application condition determination part 142 performs the total application time determination process using the similar method to the first embodiment (Step S1906), performs the application interval determination process using the similar method to the first embodiment (Step S1907), and then performs the SAR determination process (Step S1908) in order to application conditions.

Additionally, when the Beam Sat pulse application position 301 is near the heart, there is a possibility that a Beam Sat pulse is applied to a deviated position from a desired blood vessel due to the heartbeat. In order to prevent this, an application timing of each Beam Sat pulse is set so that the Beam Sat pulse application is not performed during the timing 434 affected by the heartbeat.

The timing 434 may be configured so that a period from a P wave to a T wave of the electrocardiographic waveform is detected and determined by the application condition determination part 142. Also, the reception part 141 may be configured so as to display the UI shown in FIG. 18 and receive settings by a user.

By adding the above processes, a stable suppression effect can be obtained even in electrocardiographic synchronization. This method can be applied also to a case where a respiratory cycle is considerably short.

DESCRIPTION OF REFERENCE NUMERALS

100: MRI apparatus
101: object
102: static magnetic field generating magnet
103: gradient magnetic field coil
104: transmission coil
105: reception coil
106: gradient magnetic field power source
107: RF transmission unit
108: signal detection unit
109: signal processing unit
110: sequencer
111: bed
120: control unit
121: display unit
122: operation unit
123: storage unit
124: body motion detection device
130: imaging section
140: imaging sequence generation section
141: reception part
142: application condition determination part
150: body motion detection section
160: adoption/rejection determination section
170: flow velocity calculation section
180: suppression range calculation section
210: slice selective excitation sequence
211: RF pulse
212: slice selective gradient magnetic field
220: 2D RF sequence
221: 2D RF pulse
222: vibration gradient magnetic field pulse
223: crusher gradient magnetic field pulse
301: Beam Sat pulse application position
302: region to be suppressed
303: region to be suppressed insufficiently
311: non-suppression region
321: suppression range
350: positioning image
360: Beam Sat pulse setting screen display example
400: pulse sequence
401: respiratory waveform
402: IR pulse application timing
403: TI
405: main imaging start timing
406: main imaging execution period
407: spare time
408: Beam Sat pulse application start timing
409: Beam Sat pulse application end timing
411: total application time
412: application interval
413: application times
414: amplitude
415: pulse width
421: IR pulse
422: Beam Sat pulse
422a: Beam Sat pulse
422b: Beam Sat pulse
422c: Beam Sat pulse
422d: Beam Sat pulse
423: main imaging
424: pre-pulse
431: electrocardiographic waveform
432: cardiac cycle
434: timing affected by the heartbeat
432: cycle
435: synchronization cycle
501: starting point
502: end point
503: blood vessel
504: flat plane
505: distance
507: intersection plane
508: gravity center

The invention claimed is:

1. A magnetic resonance imaging apparatus including:
   an imaging sequence generation section configured to apply imaging conditions to a predetermined pulse sequence to generate an imaging sequence; and
   an imaging section configured to collect echo signals from an imaging region according to the imaging sequence to reconstruct an image from the echo signals,
   wherein the predetermined pulse sequence includes an IR (Inversion Recovery) pulse and a plurality of two-dimensional selective high-frequency pulses,
   wherein the imaging conditions include application conditions of the plurality of two-dimensional selective high-frequency pulses,
   wherein the imaging sequence generation section includes an application condition determination part that determines whether or not set application conditions suppress blood signals that are the echo signals from blood in a targeted blood vessel, wherein in response to the echo signals are suppressed, the set application conditions are determined as applied application conditions that are the application conditions to be applied to the imaging sequence, and wherein in response to the echo signals are not suppressed, the set application conditions changed to suppress the blood signals are determined as the applied application conditions.

2. The magnetic resonance imaging apparatus according to claim 1, wherein the application conditions include a total application time and an application interval of the plurality of two-dimensional selective high-frequency pulses as well as an amplitude and a pulse width of each of the plurality of two-dimensional selective high-frequency pulses.

3. The magnetic resonance imaging apparatus according to claim 2, wherein the application condition determination part determines:

the total application time so that the total application time does not exceed a predetermined period determined by a T1 recovery time of blood while suppressing the echo signals from the blood in the targeted blood vessel;

the application interval so that the blood flowing into the imaging region is continuously suppressed;

the amplitude so as not to exceed a limitation by SAR (Specific Absorption Rate); and the pulse width according to the determined amplitude while maintaining an application area of a two-dimensional selective high-frequency pulse.

4. The magnetic resonance imaging apparatus according to claim 2, further including:

a body motion detection section that detects a displacement amount by periodic body motion of an object after the peak; and an adoption/rejection determination section that determines the adoption or rejection of the echo signals collected by the imaging section according to the relationship between the displace amount and an application start timing of a two-dimensional selective high-frequency pulse specified by the applied application conditions, wherein the imaging sequence is a body motion synchronization sequence, and wherein the imaging section reconstructs the image only from the echo signals determined to be adopted by the adoption/rejection determination section.

5. The magnetic resonance imaging apparatus according to claim 4, wherein the adoption/rejection determination section determines the echo signals obtained in the imaging sequence to be adopted when the displace amount at the application start timing is equal to or less than a predetermined threshold value.

6. The magnetic resonance imaging apparatus according to claim 4, wherein the adoption/rejection determination section compares a displacement timing at which the displacement amount becomes a predetermined threshold value with the application start timing and determines echo signals obtained in the imaging sequence to be adopted when the application start timing is after the displacement timing and when the application start timing is earlier than the displacement timing and a period from the displacement timing to the application end timing of the two-dimensional selective high-frequency pulse specified by application conditions determined by the application condition determination part is longer than a predetermined period, and the imaging section starts application of the two-dimensional selective high-frequency pulse instead of the application start timing from the displacement timing when the application start timing is earlier than the displacement timing.

7. The magnetic resonance imaging apparatus according to claim 4, wherein the periodic body motion is respiratory motion, and wherein the magnetic resonance imaging apparatus further comprises a breathing instruction device that instructs an object about a breath timing.

8. The magnetic resonance imaging apparatus according to claim 3, wherein the two-dimensional selective high-frequency pulse is cyclically applied to a plurality of blood vessels, and wherein the application condition determination part determines the application interval so that blood flowing from each blood vessel is suppressed respectively in a continuous manner without interruption and considers the two-dimensional selective high-frequency pulse to be applied to all the blood vessels in order to determine the amplitude and the pulse width so as not to exceed a limitation by the SAR.

9. The magnetic resonance imaging apparatus according to claim 1, further comprising:

a flow velocity calculation section that calculates a flow velocity of the blood from the image, wherein the imaging sequence includes a predetermined spare time between an application end timing of the plurality of two-dimensional selective high-frequency pulses and a start timing of main imaging, and wherein the flow velocity calculation section calculates the flow velocity using the spare time and a length of an unsuppressed blood flow.

10. The magnetic resonance imaging apparatus according to claim 1, further comprising:

a suppression range calculation section that calculates a suppression range from a flow velocity of the blood, wherein the suppression range calculation section calculates the suppression range using the flow velocity and a T1 recovery time of the blood.

11. The magnetic resonance imaging apparatus according to claim 3, wherein the imaging sequence is a heartbeat synchronization sequence in which a plurality of heartbeats is set as one unit.

12. The magnetic resonance imaging apparatus according to claim 3, wherein the application condition determination part determines a predetermined period to be the total application time when the total application time of the set application conditions is longer than the predetermined period determined by the T1 recovery time, determines the minimum value of a period in which blood in the targeted blood vessel can be suppressed to be the total application time when the total application time of the set application conditions is equal to or less than the suppressible period, determines a moving time to be the application interval when the set application interval is larger than the moving time obtained by dividing a suppression width of the two-dimensional selective high-frequency pulse by a flow velocity, and determines the amplitude so that the number of the plurality of two-dimensional selective high-frequency pulses to be applied per unit time determined by the set application conditions is within the limitation range when exceeding the SAR limitation.

13. A magnetic resonance imaging method, comprising:

applying imaging conditions including applied application conditions to a predetermined pulse sequence to generate an imaging sequence;

collecting echo signals from an imaging region according to the imaging sequence to reconstruct an image from the echo signals;

determining whether or not set application conditions suppress blood signals that are the echo signals from blood in a targeted blood vessel;

in response to the echo signals are suppressed, determining the set application conditions as applied application conditions that are the application conditions to be applied to an imaging sequence; and in response to the echo signals are not suppressed, determining the set application conditions changed to suppress the blood signals as the applied application conditions;

wherein the predetermined pulse sequence includes an IR (Inversion Recovery) pulse and a plurality of two-dimensional selective high-frequency pulses.

14. The magnetic resonance imaging method according to claim 13, wherein the application conditions includes a total application time and an application interval of the plurality of the two-dimensional selective high-frequency pulses as well as an amplitude and a pulse width of each of the plurality of two-dimensional selective high-frequency pulses, and wherein the amplitude is determined so as not to exceed a limitation by SAR (Specific Absorption Rate) and the pulse width is determined according to the determined amplitude while maintaining an application area of a two-dimensional selective high-frequency pulse as the applied application conditions.

* * * * *